United States Patent
Economides et al.

(10) Patent No.: US 11,319,557 B2
(45) Date of Patent: *May 3, 2022

(54) MULTIFUNCTIONAL ALLELES

(71) Applicant: REGENERON PHARMACEUTICALS, INC., Tarrytown, NY (US)

(72) Inventors: Aris N. Economides, Tarrytown, NY (US); Andrew J. Murphy, Croton-on-Hudson, NY (US); Peter Matthew Lengyel, Brooklyn, NY (US); Peter H. A. Yang, Tarrytown, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 59 days.

This patent is subject to a terminal disclaimer.

(21) Appl. No.: 16/459,236

(22) Filed: Jul. 1, 2019

(65) Prior Publication Data

US 2019/0390230 A1 Dec. 26, 2019

Related U.S. Application Data

(63) Continuation of application No. 13/940,609, filed on Jul. 12, 2013, now Pat. No. 10,392,633, which is a continuation of application No. 12/915,447, filed on Oct. 29, 2010, now abandoned.

(60) Provisional application No. 61/256,078, filed on Oct. 29, 2009.

(51) Int. Cl.
*C12N 15/90* (2006.01)
*C12N 15/63* (2006.01)
*C12N 9/00* (2006.01)

(52) U.S. Cl.
CPC ............ *C12N 15/907* (2013.01); *C12N 9/00* (2013.01); *C12N 15/63* (2013.01); *A01K 2217/15* (2013.01); *A01K 2217/20* (2013.01); *C12N 2800/30* (2013.01); *C12N 2800/60* (2013.01); *C12N 2840/44* (2013.01)

(58) Field of Classification Search
CPC .. C12N 15/907; C12N 15/63; C12N 2800/30; C12N 2800/60; C12N 2840/44; A01K 2217/15; A01K 2217/20
See application file for complete search history.

(56) References Cited

U.S. PATENT DOCUMENTS

| | | | |
|---|---|---|---|
| 6,586,251 B2 | 7/2003 | Economides et al. | |
| 7,074,611 B2 | 7/2006 | Chambon et al. | |
| 7,205,148 B2 | 4/2007 | Economides et al. | |
| 7,473,557 B2 | 1/2009 | Economides et al. | |
| 10,392,633 B2 * | 8/2019 | Economides | C12N 15/63 |
| 2003/0159160 A1 | 8/2003 | Chambon et al. | |
| 2004/0244071 A1 | 12/2004 | Chambron et al. | |
| 2006/0064769 A1 | 3/2006 | Jones et al. | |
| 2007/0275466 A1 | 11/2007 | Economides et al. | |
| 2009/0113561 A1* | 4/2009 | Von Melchner | C12N 15/1051 800/3 |
| 2011/0104799 A1 | 5/2011 | Economides et al. | |
| 2013/0302899 A1 | 11/2013 | Economides et al. | |

FOREIGN PATENT DOCUMENTS

| | | | |
|---|---|---|---|
| EP | 1383891 B1 | 12/2005 | |
| EP | 1662005 A1 | 5/2006 | |
| EP | 1815001 B1 | 2/2011 | |
| EP | 2494047 B1 | 1/2017 | |
| EP | 3147362 A1 | 3/2017 | |
| JP | 2004-536556 A | 12/2004 | |
| WO | WO 2001029208 A1 | 4/2001 | |
| WO | WO 200236789 A2 | 5/2002 | |
| WO | WO 2002040685 A2 | 5/2002 | |
| WO | WO-02088353 A2 * | 11/2002 | ............. C12N 15/63 |
| WO | WO 2002088353 A2 | 11/2002 | |
| WO | WO 2005001087 A2 | 1/2005 | |
| WO | WO 2006056617 A1 | 6/2006 | |
| WO | WO 2011059799 A1 | 5/2011 | |

OTHER PUBLICATIONS

Cruz Transgenic Research, 532-521 (Year: 2005).*
Schntitgen F, et al. Genomewide production of multipurpose alleles for the functional analysis of the mouse genome. Proc Natl Acad Sci USA 102(20):7221-7226. (Year: 2005).*
Cruz, et al., "Conditionals by inversion (COINs): A high-throughput method for engineering conditional alleles & hprt as a test locus," Transgenic Research, 14(4): 520-521, Aug. 2005.
Raymond, et al., High-efficiency FLP and C31 site-specific recombination in mammalian cells, Plos ONE, 1(162e): 1-4, 2007.
Schnutgen, et al., "A directional strategy for monitoring Cre-mediated recombination at the cellular level in the mouse," Nature Biotechnology, 21: 562-565, 2003.

(Continued)

*Primary Examiner* — Anoop K Singh
(74) *Attorney, Agent, or Firm* — Yongjin Choi; Alston & Bird LLP

(57) ABSTRACT

Nucleic acid constructs and methods for rendering modifications to a genome are provided, wherein the modifications comprise null alleles, conditional alleles and null alleles comprising COINs. Multifunctional alleles (MFA) are provided, as well as methods for making them, which afford the ability in a single targeting to introduce an allele that can be used to generate a null allele, a conditional allele, or an allele that is a null allele and that further includes a COIN. MFAs comprise pairs of cognate recombinase recognition sites, an actuating sequence and/or a drug selection cassette, and a nucleotide sequence of interest, and a COIN, wherein upon action of a recombinase a conditional allele with a COIN is formed. In a further embodiment, action of a second recombinase forms an allele that contains only a COIN in sense orientation. In a further embodiment, action by a third recombinase forms an allele that contains only the actuating sequence in sense orientation.

15 Claims, 18 Drawing Sheets

(56) References Cited

OTHER PUBLICATIONS

Testa, et al., "A reliable lacZ expression reporter cassette for multipurpose, knockout-first alleles," Genesis, 38: 151-158, 2004.
Schnutgen, et al., "Genomewide production of multipurpose alleles for the functional analysis of the mouse genome," Proc. Natl. Acad. Sci USA, 102(20): 7221-7226, 2005.
Schnutgen, et al., "Enhanced gene trapping in mouse embryonic stem cells," Nucleic Acids Research, 36(20): e133, 2008.
Schnutgen, Conditional gene trapping. European conditional mouse mutagenesis program (EuCOMM) training course, Jul. 6, 2007.
International Search Report for PCT US2010/0054654, dated Jan. 24, 2011, 4 pages.
Guan, et al., "A review of current large-scale mouse knockout efforts," Genesis, 48(2): 73-75, 2010.
Schebelle, et al., "Efficient conditional and promoter-specific in vivo expression of cDNAs of choice by taking advantage of recombinase-mediated cassette exchange using FlEx gene traps," Nucleic Acids Res., 38(9): e106, 2010.
Schnutgen, et al., Adopting the good reFLEXes when generating conditional alterations in the mouse genome, Transgenic Res., 16(4): 405-413, 2007.
Xin, et al., "Gene trap and gene inversion methods for conditional gene inactivation in the mouse," Nucleic Acids Res., 33(2): e14, 2005.
Buchholz, et al., "Different thermostabilities of FLP and Cre recombinases: implications for applied site-specific recombination," Nucleic Acids Research, 24(21): 4256-4262, 1996.
U.S. Appl. No. 12/915,447, Final Office Action dated Jan. 16, 2013.
U.S. Appl. No. 12/915,447, Non-Final Office Action dated Jun. 7, 2012.
U.S. Appl. No. 12/915,447, Requirement for Restriction/Election dated Mar. 28, 2012.
U.S. Appl. No. 13/940,609, Non-Final Office Action dated Sep. 15, 2015.
U.S. Appl. No. 13/940,609, Requirement for Restriction/Election dated Jul. 8, 2015.
PCT Written Opinion of the International Searching Authority for application PCT/US2010/054654 dated Jan. 24, 2011.
PCT International Preliminary Report on Patentability for application PCT/US2010/054654 dated May 1, 2012.
Valenzuela, et al., "High-throughput engineering of the mouse genome coupled with high-resolution expression analysis," Nature Biotechnology, 21(6): 652-659, Jun. 1, 2003.
Doetschman, et al., "Targetted correction of a mutant HPRT gene in mouse embryonic stem cells," Nature, 330(6148): 576-578, Dec. 10, 1987.
Sauer, et al., "Site-specific DNA recombination in mammalian cells by the Cre recombinase of bacteriophage," Proceedings of the National Academy of Sciences USA, 85(14), 5166-5170, Jul. 1988.
Economides et al., "Conditionals by inversion provide a universal method for the generation of conditional alleles," Proceedings of the National Academy of Sciences, 110(34):E3179-E3188, (2013).
EPO European Search Report for application EP16196614 dated Jan. 25, 2017.
U.S. Appl. No. 13/940,609, Final Office Action dated Mar. 21, 2016.
U.S. Appl. No. 13/940,609, Advisory Action dated Jun. 27, 2016.
U.S. Appl. No. 13/940,609, Advisory Action dated Sep. 26, 2016.
U.S. Appl. No. 13/940,609, Examiner Initiated Interview Summary dated Jun. 27, 2016.
U.S. Appl. No. 13/940,609, Applicant Initiated Interview Summary dated Sep. 26, 2016.
U.S. Appl. No. 12/915,447, Applicant Initiated Interview Summary dated Sep. 13, 2013.
U.S. Appl. No. 13/940,609, Non-Final Office Action dated Jun. 28, 2017.
Lodish, et al., "Section 11.2 Processing of Eukaryotic mRNA," Molecular Cell Biology 4th Edition, W.H. Freeman, New York, (2000). [Retrieved from the Internet Sep. 28, 2017: https://www.ncbi.nlm.nih.gov/books/NBK21563/].
Zambrowicz, et al., "Disruption of overlapping transcripts in the ROSA βgeo 26 gene trap strain leads to widespread expression of β-galactosidase in mouse embryos and hematopoietic cells," Proc. Natl. Acad. Sci. USA, 94:3789-3794, (1997).
Madisen et al., "A robust and high-throughput Cre reporting and characterization system forthe whole mouse brain," Nat. Neurosci., 13(1):133-140, (2010) (*author manuscript; available in PMC Jul. 1, 2010*).
U.S. Appl. No. 13/940,609, Non-Final Office Action dated Jan. 12, 2018.
Meyers et al., "An Fgf8 mutant allelic series generated by Cre- and Flp-mediated recombination," Nature Genetics, 18(2):136-141, (1998).
Mandalos, et al., "Application of a Novel Strategy of Engineering Conditional Alleles to a Single Exon Gene, Sox2," *PLOS ONE*, vol. 7, Issue 9, e45768, (Sep. 2012).
U.S. Appl. No. 13/940,609, Final Office Action dated Aug. 15, 2018.
Murphy, "BAC-based Modifications of the Mouse Genome: The Big and the Backward," Regeneron Pharmaceuticals, Inc. VP Target Discovery, *Wellcome Trust Advanced Course: Genetic Manipulation of ES Cells*, Hinxton, UK, (Nov. 3, 2009).
U.S. Appl. No. 13/940,609, Notice of Allowance and Interview Summary dated Apr. 5, 2019.

\* cited by examiner

MULTIFUNCTIONAL ALLELES

CROSS REFERENCE TO RELATED APPLICATIONS

This application is a continuation of U.S. application Ser. No. 13/940,609 filed Jul. 12, 2013, now U.S. Pat. No. 10,392,633, which is a continuation of U.S. application Ser. No. 12/915,447 filed Oct. 29, 2010, which claims the benefit under 35 USC § 119(e) of U.S. Provisional Application No. 61/256,078 filed Oct. 29, 2009, each of which are herein incorporated by reference.

FIELD OF INVENTION

The invention relates to nucleic acid constructs for modifying genomes, including knockout constructs and constructs for placing COINs in a genome. Genetically modified non-human animals are included, e.g., genetically modified mice having genes or nucleic acid elements arrayed with selected recombinase recognition sites that allow for deletion or inversion of the genes or nucleic acid elements to form null alleles, selectable alleles, reporting alleles, and/or conditional alleles in non-human animals, e.g., in mice and rats.

BACKGROUND

Typically, knockouts are made by homologously replacing a target gene with another sequence of choice, usually a reporter and a selection cassette, where the latter is preferably flanked by site-specific recombinase sites to empower removal of the selection cassette via the action of the cognate site-specific recombinase. The selection cassette can be subsequently removed either by treating cells with the corresponding cognate recombinase or by breeding mouse progeny to a "deletor" strain. For example, in the case of floxed alleles (where the sequence of interest is flanked by loxP sites), the cognate recombinase is Cre, and what remains in the genome is a single loxP site and the reporter.

A related strategy has been traditionally employed to generate conditional-null alleles. This involves flanking part of the gene of interest with site-specific recombinase recognition sites (such as lox for Cre, and FRT for Flp) in a manner such that upon action of the cognate recombinase, the region flanked by the site-specific recombinase recognition sites is deleted and the resulting allele is a null allele.

Although attempts have been made to incorporate both a null and a conditional functionality in one targeting vector and to accomplish building the corresponding modified alleles in a single targeting step, the methods that have resulted from such attempts have several drawbacks and have had mixed success. These drawbacks include, for example, lack of true functionality (i.e., the null version is not a true null, the conditional allele is not a true conditional, lack of reporter function, etc.) or inability to realize a practical working allele with the desired features.

Therefore, there is a need in the art for generating genetically modified organisms via targeting where the engineered loci are multifunctional loci, for example, a true KO-first allele and then a conditional-null or other conditional-mutant allele.

SUMMARY

Figure 1:
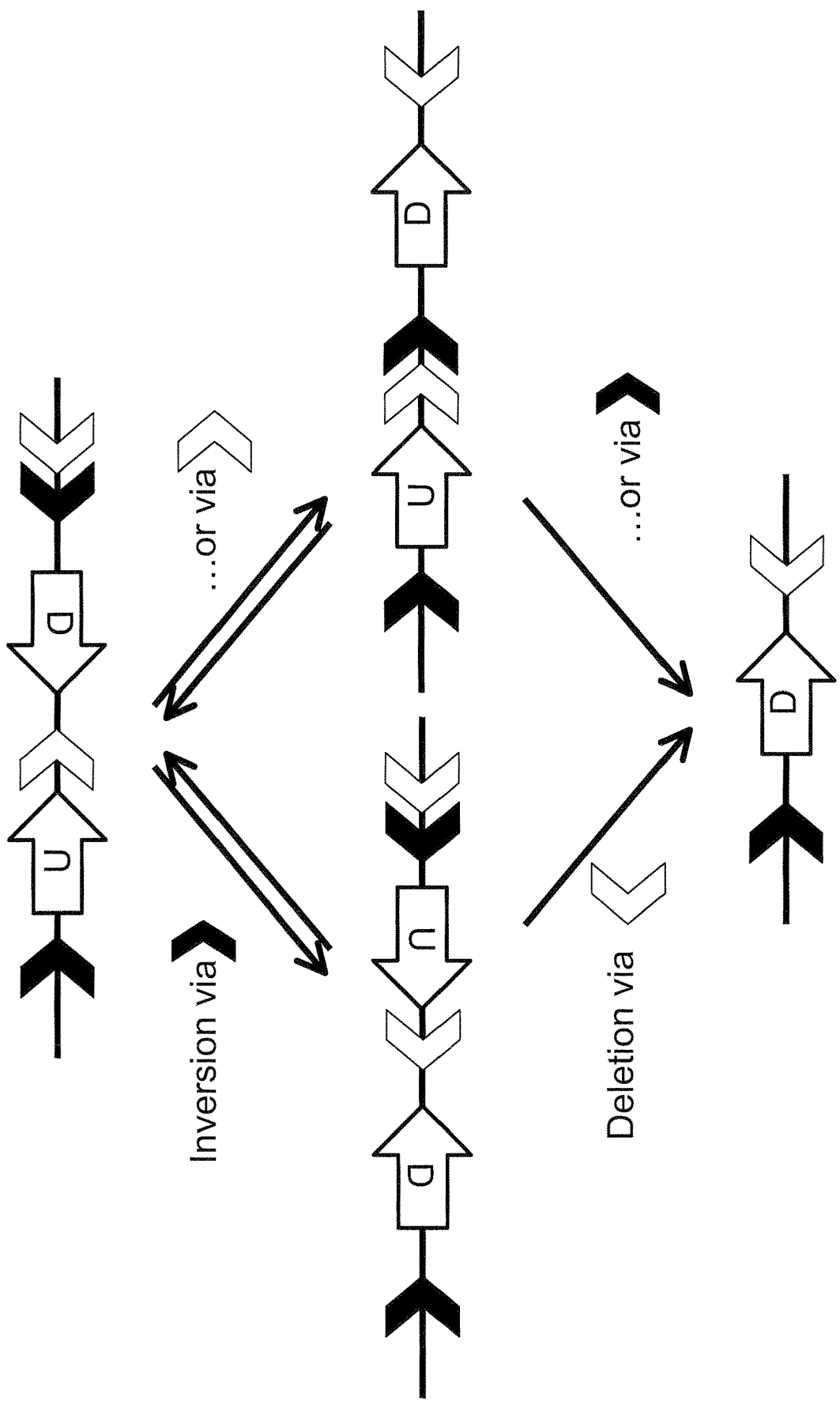
FIG. 1 illustrates use of recombinase recognition sites to simultaneously delete one element (U) and invert another (D).

Methods and compositions for making null alleles and conditional alleles, and alleles that combine null and COIN features, are provided. In various embodiments, methods and compositions are provided for engineering multifunctional alleles into a genome in a single targeting step. Methods and compositions for knockout complementation analysis in genetically modified nonhuman animals are provided, including methods that comprise a single targeting step.

In one aspect, a modified allele is provided, comprising a 3' splice region and splice acceptor, an actuating sequence 3' with respect to the splice acceptor, and a nucleotide sequence of interest (NSI) 3' with respect to the actuating sequence, wherein the NSI is in antisense orientation with respect to the target gene (or the locus being modified, or with respect to the actuating sequence).

In one embodiment, the actuating sequence is selected from a microRNA, a transcriptional stop signal (such as a polyadenylation region), a nucleotide sequence encoding a cDNA, or any combinations thereof, and may include regulatory elements such as operators, enhancers, and insulators. In a specific embodiment, the cDNA encodes a reporter (e.g., encodes for LacZ). In one embodiment, the actuating sequence comprises an exon. In a specific embodiment, the exon is the 5'-most exon of a locus.

In one embodiment, the NSI comprises an exon. In one embodiment, the NSI comprises an exon and neighboring intronic sequence. In a specific embodiment, the flanking exon is flanked 5' and 3' with intronic sequence. In one embodiment, the nucleotide sequence comprises two or more exons, and in a specific embodiment comprises intronic sequence(s). In another embodiment, the NSI lacks an exon, or lacks a fragment of an exon.

In one embodiment, the modified allele comprises a COIN. In one embodiment, the COIN is 3' with respect to the NSI; in another embodiment, the COIN is 5' with respect to the NSI.

In one embodiment, the COIN is selected from a reporter, a gene trap-like element (GT-like element), and a gene trap-like reporter (GT-like reporter). In a specific embodiment, the GT-like element is selected from SA-drug resistance cDNA-polyA. In a specific embodiment, the GT-like reporter is selected from SA-reporter-polyA.

In one embodiment, the COIN comprises a 3' splice region. In a specific embodiment, the 3' splice region is followed by a sequence selected from a cDNA, an exon-intron sequence, a microRNA, a microRNA cluster, a small RNA, a codon-skipping element, an IRES, a polyadenylation sequence, or any combination thereof. In a specific embodiment, the small RNA is a mirtron. In a specific embodiment, the codon-skipping element is T2A, E2A, or F2A.

In one embodiment, the modified allele comprises a drug selection cassette (DSC).

In one embodiment, the modified allele is on a targeting construct that comprises an upstream and a downstream homology arm. In one embodiment, at least one homology arm is a mouse homology arm. In a specific embodiment, both homology arms are mouse homology arms.

In one embodiment, the modified allele comprises, from 5' to 3', a splice acceptor, an actuating sequence, a DSC, a NSI and a COIN wherein the nucleotide sequence of interest and the COIN are both in antisense orientation with respect to the actuating sequence, and five pairs of site-specific recombinase recognition sites. In one embodiment, the modified allele, upon exposure to a first site-specific recombinase that independently recognizes and inverts sequence between a first pair of the site-specific recombinase recognition sites and deletes a sequence between a second pair of the site-specific recombinase recognition sites, results in an allele that comprises the NSI in sense orientation for transcription, that lacks the DSC, and that comprises the COIN in antisense orientation. In one embodiment, the modified allele comprises third and fourth site-specific recombinase recognition sites arranged such that further exposure of the allele to a second recombinase that independently recognizes the third and fourth site-specific recombinase recognition sites results in deleting the NSI and placing the COIN in sense orientation for transcription.

In one aspect, a nucleic acid construct is provided that comprises (a) a reporter in sense orientation and a DSC in a suitable orientation of choice, and in antisense orientation a NSI and a COIN; (b) five pairs of site specific recombinase recognition sites, wherein the five pairs of recombinase recognition sites are recognized by no more than three recombinases; wherein upon treatment of the nucleic acid construct with a first recombinase, a modified allele is formed wherein (i) the NSI is placed in sense orientation, (ii) the COIN remains in antisense orientation, (iii) the reporter and the DSC are deleted, and, (iv) the modified allele upon treatment with a second recombinase inverts and/or deletes the NSI and places the COIN in sense orientation.

In one embodiment, the five pairs of site-specific recombinase recognition sites are FRT3, Rox, FRT, loxP, and lox2372 pairs.

In one embodiment, the first recombinase is a Flp recombinase, and the second recombinase is a Cre recombinase.

In one embodiment, the modified allele upon treatment with the second recombinase results in an allele that cannot be deleted or inverted by the first or the second recombinase.

In one embodiment, the nucleotide sequence of interest is a wild-type exon of a gene. In another embodiment, the NSI is an exon of a gene having one or more nucleic acid substitutions, deletions, or additions.

In one embodiment, the NSI is a wild-type exon plus intronic flanking of a gene. In another embodiment, the NSI is an exon plus neighboring intronic sequence of a gene having one or more nucleic acid substitutions, deletions, or additions.

In one embodiment, the NSI is a wild type intron of a gene. In another embodiment, the NSI is an intron of a gene having one or more nucleic acid substitutions, deletions, or additions.

In one embodiment, the COIN comprises an exon or exons of a gene that comprises one or more nucleic acid substitutions, deletions, or additions. In a specific embodiment, the COIN comprises an exon of a mammal. In a specific embodiment, the mammal is a human, mouse, monkey, or rat.

In one embodiment, the COIN comprises a 3' splice region. In a specific embodiment, the 3' splice region is followed by a sequence selected from a cDNA, an exon-intron sequence, a microRNA, a microRNA cluster, a small RNA, a codon-skipping element, an IRES, a polyadenylation sequence, and a combination thereof.

In a specific embodiment, the small RNA is a mirtron. In a specific embodiment, the codon-skipping element is a T2A.

In one embodiment, the COIN is selected from a reporter, a gene trap-like element (GT-like element), and a gene trap-like reporter (GT-like reporter). In a specific embodiment, the GT-like element is selected from SA-drug resistance cDNA-polyA. In a specific embodiment, the GT-like reporter is selected from SA-reporter-polyA.

In one embodiment, the construct further comprises an upstream and a downstream homology arm. In one embodiment, the upstream and the downstream homology arm are mouse or rat homology arms. In a specific embodiment, the homology arms are mouse homology arms and the NSI comprises a human sequence. In a specific embodiment, the human sequence comprises a human exon that is a human homolog of a mouse exon.

In one embodiment the reporter is selected from: a fluorescent protein, a luminescent protein, or an enzyme. In a specific embodiment, the reporter is selected from GFP, eGFP, CFP, YFP, eYFP, BFP, eBFP, DsRed, MmGFP, luciferase, LacZ, and alkaline phosphatase.

In one embodiment the DSC comprises a sequence that encodes an activity selected from neomycin phosphotransferase ($neo^r$), hygromycin B phosphotransferase ($hyg^r$), puromycin-N-acetyltransferase ($puro^r$), blasticidin S deaminase ($bsr^r$), xanthine/guanine phosphoribosyl transferase (gpt), nourseothricin acetyltransferase (nat1), and Herpes simplex virus thymidine kinase (HSV-tk).

In one aspect, a nucleic acid construct is provided that comprises an actuating sequence that comprises a 3' splice acceptor followed by a reporter in sense orientation, DSC in a suitable orientation of choice, a NSI in antisense orientation, and a COIN in antisense orientation, wherein the actuating sequence and reporter is flanked upstream by a recombinase recognition site R1, a recombinase recognition site R2 is disposed between the reporter and the DSC, a recombinase site R3 is disposed between the DSC and the nucleotide sequence of interest, a recombinase site R4 is disposed between the site R3 and the NSI, a recombinase site R5 is disposed between the NSI and the COIN, a recombinase site R1' is disposed between site R5 and the COIN, a recombinase site R3' is disposed between R1' and the COIN, a recombination site R5' is disposed downstream of the COIN, a recombination site R4' is disposed downstream of site R5', and a recombination site R2' is disposed downstream of site R4'; wherein R1 and R1' are in opposite orientation, R2 and R2' are in the same orientation, R3 and R3' are in opposite orientation, R4 and R4' are in the same orientation, and R5 and R5' are in the same orientation.

In one embodiment, the reporter is followed by a polyadenylation region.

In one embodiment, R1 and R1' are recognized by a recombinase that recognizes R3 and R3'. In one embodiment, R4 and R4' are recognized by a recombinase that recognizes R5 and R5'. In one embodiment, R2 and R2' are not recognized by any recombinase that recognizes R1/R1', R3/R3', R4/R4', or R5/R5'. In one embodiment, R1 and R1', R3 and R3', and R2 and R2' are not recognized by any recombinase that recognizes R4 and R4', and R5 and R5'. In one embodiment, R4 and R4', R5 and R5', and R2 and R2' are not recognized by any recombinase that recognizes R1 and R1' and R3 and R3'.

In one embodiment, treatment with a single recombinase results in a nucleic acid construct that lacks the DSC, the NSI, and the COIN. In a specific embodiment, the resulting nucleic acid construct consists essentially of the actuating sequence, R1, and R2 or R2'. In a specific embodiment, R1 is a FRT3 site and R2 (or R2') is a Rox site.

In one embodiment, treatment with a single recombinase results in a nucleic acid construct that comprises the actuating sequence in sense orientation but that lacks the DSC, lacks the NSI, and lacks the COIN. In a specific embodiment, R2 and R2' are Rox sites, and the single recombinase is Dre recombinase.

In one embodiment, treatment with a single recombinase results in a nucleic acid construct that comprises the NSI in the antisense orientation and the COIN in antisense orientation. In one embodiment, the single recombinase is a Flp recombinase, R1 and R1' are a FRT variant sequence that does not cross-react with R3 and R3' (which are also FRT or FRT variants), R2 and R2' are Rox sequences, and R4 and R4' are loxP or lox variant sequences that do not cross-react with R5 and R5', wherein R5 and R5' are lox variant sequences.

In one embodiment, treatment with a single recombinase results in a nucleic acid construct that comprises the NSI in sense orientation and the COIN in antisense orientation. In one embodiment the single recombinase is a Flp recombinase, R1 and R1' are FRT3 sequences, R2 and R2' are Rox sequences, R3 and R3' are FRT sequences, R4 and R4' are loxP sequences, R5 and R5' are lox2372 sequences.

In one embodiment, the NSI is a wild type exon of a gene. In another embodiment, the NSI is an exon of a gene having one or more nucleic acid substitutions, deletions, or additions.

In one embodiment, the COIN comprises an exon or exons of a gene that comprises one or more nucleic acid substitutions, deletions, or additions. In a specific embodiment, the COIN comprises an exon of a mammal. In one embodiment, the mammal is a human, mouse, monkey, or rat.

In one embodiment, the construct further comprises a homology arm upstream of the construct (an upstream homology arm) and a homology arm downstream of the construct (a downstream homology arm). In one embodiment, the upstream and the downstream homology arm are mouse or rat homology arms. In a specific embodiment, the homology arms are mouse homology arms and the NSI comprises a human sequence. In a specific embodiment, the human sequence comprises a human exon homologous to a mouse exon.

In one embodiment the reporter is selected from: a fluorescent protein, a luminescent protein, or an enzyme. In a specific embodiment, the reporter is selected from GFP, eGFP, CFP, YFP, eYFP, BFP, eBFP, DsRed, MmGFP, luciferase, LacZ, and alkaline phosphatase. In one embodiment the DSC comprises a sequence that encodes an activity selected from neomycin phosphotransferase (neo$^r$), hygromycin B phosphotransferase (hyg$^r$), puromycin-N-acetyl-transferase (puro$^r$), blasticidin S deaminase (bsr$^r$), xanthine/guanine phosphoribosyl transferase (gpt), nourseothricin acetyltransferase (nat1), and Herpes simplex virus thymidine kinase (HSV-tk).

In one aspect, a nucleic acid construct for modifying a locus is provided, comprising a first, second, third, fourth, and fifth overlapping recombinable unit, wherein a recombinable unit includes a pair of cognate site-specific recombinase recognition sites, and wherein (a) the first recombinable unit is framed by recombinase sites R1 and R1' in opposite orientation (allowing inversion via R1/R1'), wherein between R1 and R1' are disposed an actuating sequence in sense orientation with respect to direction of transcription of the target gene followed by a recombinase site R2 followed by a DSC in a suitable orientation of choice followed by a recombinase site R3 followed by a recombinase site R4 followed by a NSI in antisense orientation followed by a recombinase site R5; (b) the second recombinable unit is framed by recombinase sites R2 and R2' in the same orientation (allowing deletion via R2/R2'), wherein between R2 and R2' are disposed a DSC in a suitable orientation of choice followed by R3 followed by R4 followed by the NSI in antisense orientation followed by R5 followed by R1' followed by recombinase site R3' wherein R3' is in opposite orientation with respect to R3 (enabling inversion via R3/R3'), followed by a COIN in antisense orientation, followed by R5' wherein R5' is in the same orientation with respect to R5 followed by R4' wherein R4' is in the same orientation with respect to R4; (c) the third recombinable unit is framed by recombinase sites R3 and R3' in opposite orientation (allowing inversion via R3/R3'), wherein between R3 and R3' are disposed R4, the NSI in antisense orientation followed by R5 followed by R1'; (d) the fourth recombinable unit framed by recombinase sites R4 and R4' in the same orientation, wherein between R4 and R4' are disposed the NSI in antisense orientation followed by R5 followed by R1' followed by R3' followed by the COIN in antisense orientation followed by R5' followed by R4'; and, (e) the fifth recombinable unit is framed by R5 and R5' in the same orientation, wherein between R5 and R5' are disposed R1' followed by R3' followed by the COIN in antisense orientation.

In one embodiment, R1/R1' and R3/R3' are functional with respect to the same site-specific recombinase, and said same site-specific recombinase is not functional with respect to R4/R4' and R5/R5', and R2/R2'.

In one embodiment, R4/R4' and R5/R5' are functional with respect to the same site specific recombinase, and said same site-specific recombinase is not functional with respect to R1/R1' and R3/R3', and R2/R2'.

In one embodiment, R2/R2' are functional with a recombinase, wherein said recombinase is not functional with respect to any of R1/R1', R3/R3', R4/R4', and R5/R5'.

In one embodiment R1/R1' are FRT, FRT3, loxP, or lox2372 sites. In one embodiment R3/R3' are FRT, FRT3, loxP, or lox2372 sites. In one embodiment R4/R4' are FRT, FRT3, loxP, or lox2372 sites. In one embodiment, R5/R5' are FRT, FRT3, loxP, or lox2372 sites. In one embodiment, R2/R2' are Rox sites. In one embodiment, R2/R2' are attP/attB sites.

In a specific embodiment, R1/R1' and R3/R3' are functional with a Flp recombinase. In another specific embodiment, R1/R1' and R3/R3' are functional with a Cre recombinase.

In a specific embodiment, R4/R4' and R5/R5' are functional with a Cre recombinase. In another specific embodiment, R4/R4' and R5/R5' are functional with a Flp recombinase.

In one embodiment, R2/R2' are Rox sites that are functional with a Dre recombinase. In another embodiment, R2/R2' are attP/attB sites that are functional with PhiC31 integrase (phiC31 \int).

In one embodiment the reporter is selected from: a fluorescent protein, a luminescent protein, or an enzyme. In a specific embodiment, the reporter is selected from GFP, eGFP, CFP, YFP, eYFP, BFP, eBFP, DsRed, MmGFP, luciferase, LacZ, and Alkaline Phosphatase.

In one embodiment the DSC comprises a sequence that encodes an activity selected from neomycin phosphotransferase (neo^r), hygromycin B phosphotransferase (hyg^r), puromycin-N-acetyltransferase (puro^r), blasticidin S deaminase (bsr^r), xanthine/guanine phosphoribosyl transferase (gpt), nourseothricin acetyltransferase (nat1), and Herpes simplex virus thymidine kinase (HSV-tk).

In one embodiment, the NSI is a wild-type exon of a gene. In another embodiment, the NSI is an exon of a gene having one or more nucleic acid substitutions, deletions, or additions.

In one embodiment, the COIN comprises an exon of a gene that comprises one or more nucleic acid substitutions, deletions, or additions. In a specific embodiment, the COIN comprises an exon of a human, mouse, monkey, or rat.

In one embodiment, the COIN comprises a 3' splice region. In a specific embodiment, the 3' splice region is followed by a sequence selected from a cDNA, an exon-intron sequence, a microRNA, a microRNA cluster, a small RNA, a codon-skipping element, an IRES, a polyadenylation sequence, and a combination thereof. In a specific embodiment, the small RNA is a mirtron. In a specific embodiment, the codon-skipping element is T2A, E2A, or F2A.

In one embodiment, the COIN is selected from a reporter, a gene trap-like element (GT-like element), and a gene trap-like reporter (GT-like reporter). In a specific embodiment, the GT-like element is selected from SA-drug resistance cDNA-polyA. In a specific embodiment, the GT-like reporter is selected from SA-reporter-polyA.

In one embodiment, the construct further comprises a homology arm upstream of the construct (an upstream homology arm) and a homology arm downstream of the construct (a downstream homology arm). In one embodiment, the upstream and the downstream homology arm are mouse or rat homology arms. In a specific embodiment, the homology arms are mouse homology arms and the NSI comprises a human sequence. In a specific embodiment, the human sequence comprises a human exon homologous to a mouse exon.

In one aspect, a multifunctional allele is provided comprising two or more recombinable units that are recognized by two or more different recombinases, each recombinable unit defined by a pair of compatible recombinase recognition sites that define the boundaries of the recombinable unit. Each recombinable unit comprises one or more internal recombinase recognition sites. The one or more internal recombinase recognition sites are selected such that, upon recombination by a first recombinase of a recombinable unit of the multifunctional allele, the one or more internal recombinase recognition sites within one recombinable unit then pair with one or more internal recombinase units within another recombinable unit to allow for the inversion and/or deletion by the first recombinase of a sequence that straddles two or more recombinable units of the multifunctional allele, wherein the inversion and/or deletion is possible only upon inversion of the one or more internal recombinase recognition sites.

In one embodiment, the inversion and/or deletion is accompanied by inversion of a further recombinase recognition site of the multifunctional allele, wherein inversion of the further recombinase recognition site allows for the inversion or deletion of an element of the multifunctional allele by a second recombinase.

In one aspect, a multifunctional allele is provided, comprising: (a) a first, a second, a third, a fourth, and a fifth recombinable unit, wherein each recombinable unit is bounded by compatible recombinase recognition sites and wherein the first recombinable unit overlaps the second recombinable unit, and wherein the third, fourth, and fifth recombinable units are contained within the second recombinable unit; (b) a first recombinable unit comprising a 3' splice acceptor and splice region operably linked to an actuating sequence, a DSC, and a NSI; (c) a second recombinable unit comprising the DSC, the NSI, and a COIN; (d) a third recombinable unit comprising the NSI; (e) a fourth recombinable unit comprising the NSI and the COIN; (ft a fifth recombinable unit comprising the COIN; wherein multifunctional alleles comprise a first pair of recombinase recognition sites flanking the first recombinable unit upstream and downstream that allow in a first inversion of the first recombinable unit, wherein the first inversion results in a second inversion of a recombinase site within the second recombinable unit, wherein the second inversion orients the recombinase site within the second recombinable unit so as to delete the actuating sequence and delete the DSC.

In one embodiment, a single recombinase recognizes the first pair of recombinase recognition sites and also deletes the actuating sequence and the drug selection cassette.

In one embodiment, the second inversion orients a recombination site such that following the inversion a second set of recombinase recognition sites are formed that allow deletion of the NSI and/or inversion of the COIN.

In one aspect, a nucleic acid construct is provided, comprising a MFA comprising, from 5' to 3' with respect to the direction of transcription, a COIN in antisense orientation, a NSI in antisense orientation, a DSC, and a reporter in sense orientation, wherein upon treatment of the MFA with a selected recombinase, the COIN, the NSI, and the DSC are excised and the reporter remains in sense orientation; and wherein upon an alternate treatment with a different selected recombinase, the reporter and the DSC are excised, the COIN remains in antisense orientation, and the NSI is placed in sense orientation, such that upon a further treatment with yet another different selected recombinase, the NSI is excised and the COIN is placed in sense orientation.

In one embodiment, the MFA comprises a first recombinable unit, a second recombinable unit, and a third recombinable unit, wherein the first recombinable unit overlaps the second and third recombinable units, and wherein the second recombinable unit overlaps the first and third recombinable units.

In one embodiment, the first recombinable unit comprises a COIN in inverse (antisense) orientation and an NSI in inverse orientation, wherein the recombinable unit is flanked upstream of the COIN and downstream of the NSI by compatible recombinase sites R2 and R2' oriented to direct a deletion; the second recombinable unit overlaps the first recombinable unit, and the second recombinable unit is recombinable by action of a recombinase on a recombination site upstream of the DSC and a recombination site downstream of the reporter, wherein the recombination sites are oriented to direct an inversion, and wherein the recombination site upstream of the DSC is followed by a sequence comprising the NSI. In a specific embodiment, the MFA comprises, from 5' to 3' with respect to orientation on a sense strand, a first recombinase site R1, a second recombinase site R2, a third recombinase site R3, the COIN in antisense orientation, a fourth recombinase site R4, a fifth recombinase site R5, a sixth recombinase site R3' that is compatible with R3 and oriented to direct a deletion of sequence between R3 and R3', the NSI in antisense orientation, a seventh recombinase site R2' that is compatible with R2 and oriented to direct a deletion of sequence between R2 and R2', an eighth recombinase site R4', a DSC, a ninth recombinase site R1' that is compatible with R1 and oriented to direct a deletion of sequence between R1 and R1', a reporter in sense orientation, and a tenth recombinase site R5' that is compatible with R5 and oriented to direct an inversion of sequence between R5 and R5'.

Figure 11:
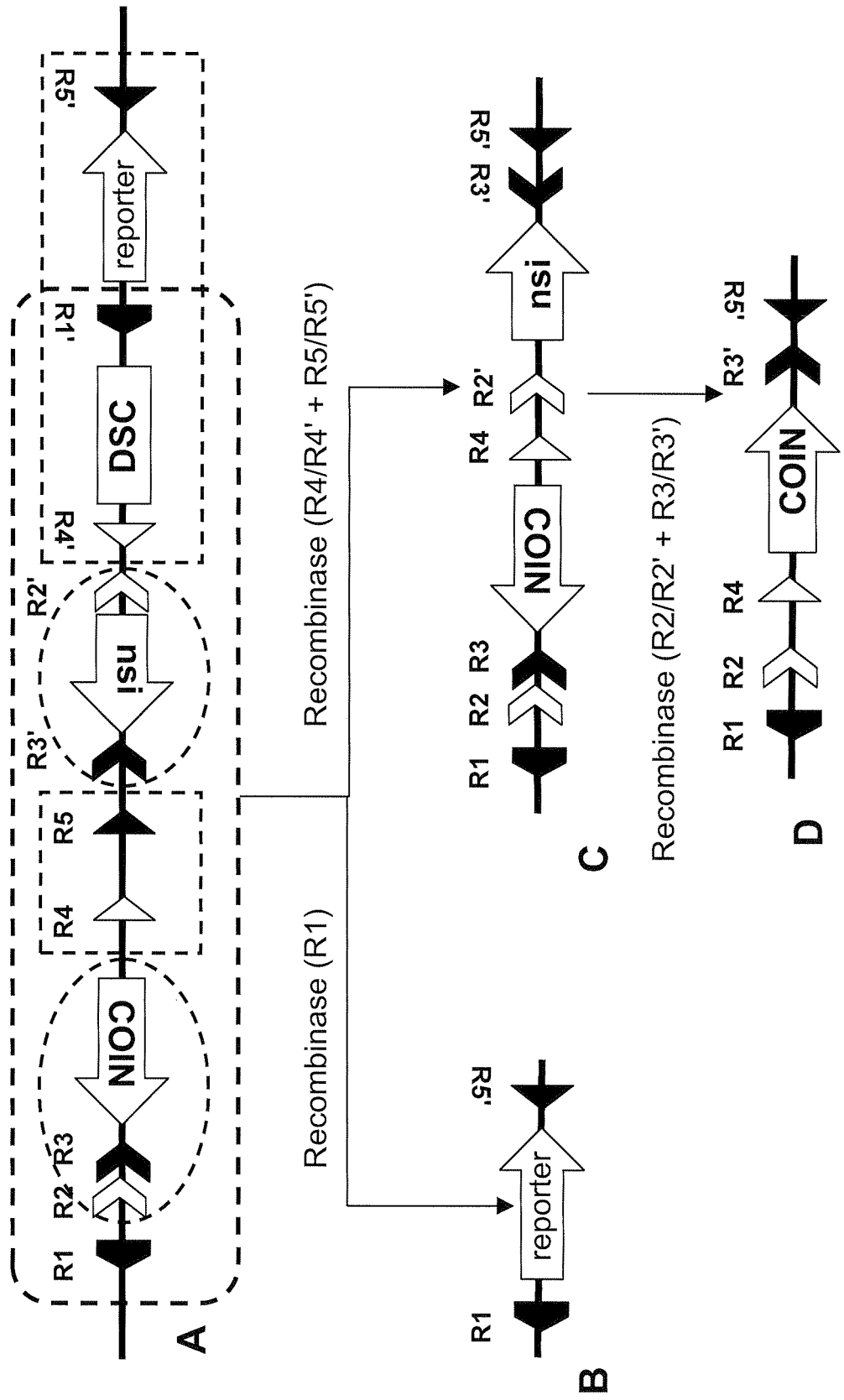
FIG. 11 illustrates an embodiment of an MFA, showing certain overlapping recombinable units (A) and resulting alleles that are generated by the action of a first recombinase (B) or a second (C) and third (D) recombinase.

In a specific embodiment, R1/R1' are Rox sites, R2/R2' are loxP sites, R3/R3' are lox 2372 sites, R4/R4' are FRT sites, and R5/R5' are FRT3 sites. In a specific embodiment, the MFA comprises a placement of recombinase sites and COIN, NSI, DSC, and reporter as shown in FIG. 11, Panel A. In a specific embodiment, upon exposure to a single recombinase that recognizes R1/R1', an allele as shown in FIG. 11, Panel B is formed. In a specific embodiment, upon exposure to a single recombinase that recognizes R4/R4' and R5/R5', an allele as shown in FIG. 11, Panel C is formed. In a specific embodiment, upon exposure of the allele of FIG. 11, Panel C to a further recombinase that recognizes R2/R2' and R3/R3', an allele as shown in FIG. 11, Panel D is formed.

In one aspect, a nucleic acid construct is provided, comprising a MFA comprising, from 5' to 3' with respect to the direction of transcription, a NSI in antisense orientation, a DSC, a reporter in sense orientation, and a COIN in antisense orientation; wherein upon treatment of the MFA with a selected recombinase, the NSI and the DSC are excised, the reporter remains in sense orientation, and the COIN remains in antisense orientation; and wherein upon an alternate treatment with a different selected recombinase, the DSC and the reporter are excised, and the NSI is placed in sense orientation and the COIN is in antisense orientation, and wherein following the alternate treatment with the different selected recombinase, the allele is treated with yet another different selected recombinase resulting in NSI excision and placement of the COIN in sense orientation.

In one embodiment, the MFA comprises a first recombinable unit, a second recombinable unit, and a third recombinable unit, wherein the first recombinable unit overlaps the second and third recombinable units, and wherein the second recombinable unit overlaps the first and third recombinable units. In one embodiment, the first recombinable unit comprises a DSC and a reporter in sense orientation, wherein the recombinable unit is flanked upstream of the DSC by recombination sites R2 followed by R3, and flanked downstream of the reporter by recombinase site R3' wherein R2/R3' are oriented to direct an inversion, and wherein the DSC is preceded by R2' oriented with respect to R2 to direct an inversion; the second recombinable unit is flanked upstream of the antisense NSI by R4 and flanked downstream of the antisense COIN by R4' wherein R4/R4' are oriented to direct an excision, and wherein the second recombinable unit includes the DSC and reporter; and the third recombinable unit is flanked upstream by R1 and downstream by R1', wherein R1/R1' are oriented to direct an excision, wherein upstream and adjacent to R1' is the DSC and wherein downstream of and adjacent to R1 is R2. In a specific embodiment, the MFA comprises from 5' to 3', with respect to the direction of transcription, R1, R2, R3, R4, the NSI in antisense orientation, R5, R2' wherein R2/R2' are oriented to direct an inversion, the DSC, R1' wherein R1/R1' are oriented to direct an excision, the reporter gene, R3' wherein R3/R3' are oriented to direct an inversion, the COIN in antisense orientation, R5' wherein R5/R5' are oriented to direct an excision, and R4' wherein R4/R4' are oriented to direct an excision.

In a specific embodiment, R1/R1' are Rox sites, R2/R2' are FRT or FRT3 sites, R3/R3' are FRT or FRT3 sites that are not the same as R2/R2', R4/R4' are lox2372 sites or loxP sites, and R5/R5' are lox2372 sites or loxP sites that are not the same as R4/R4'.

Figure 12:
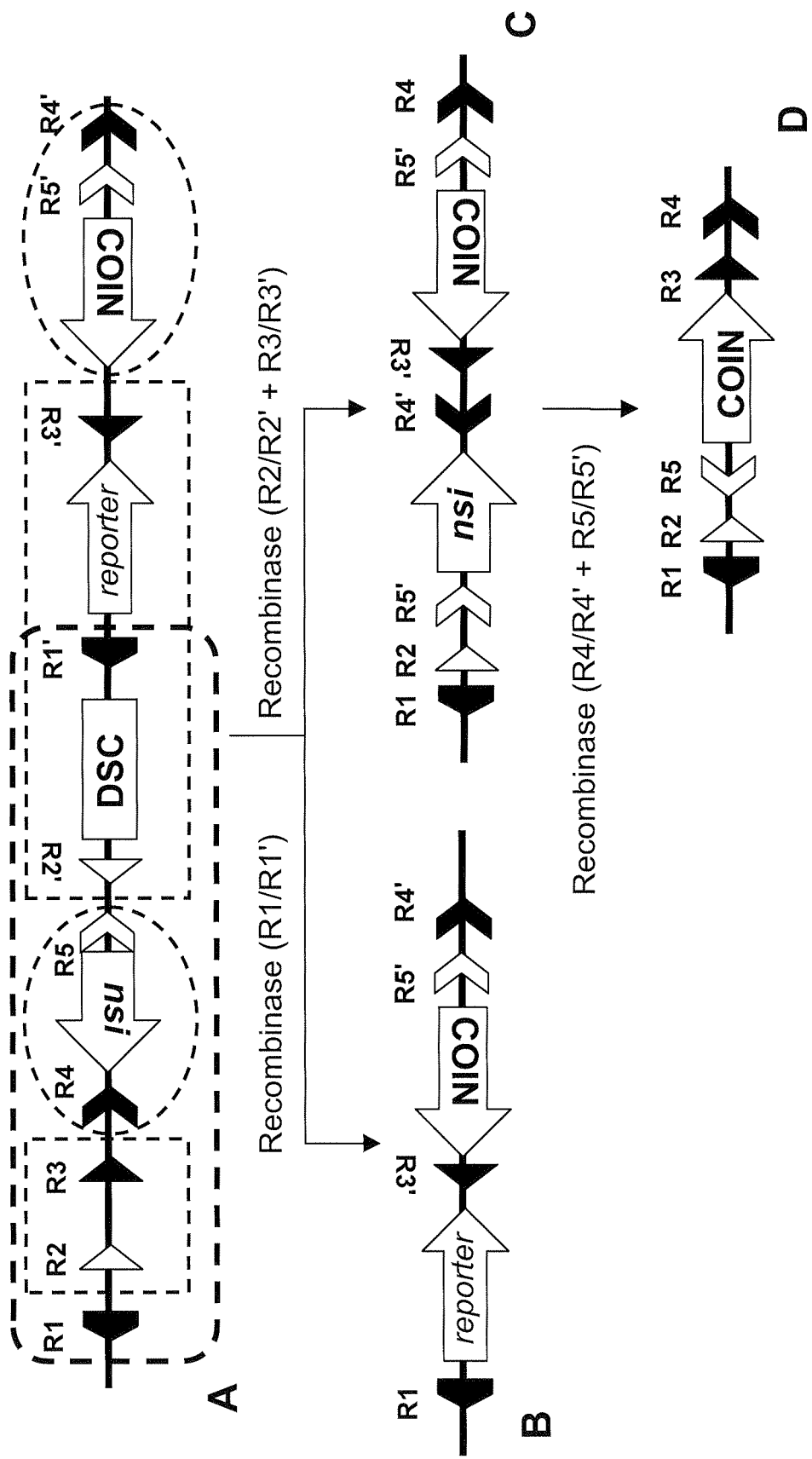
FIG. 12 illustrates an embodiment of an MFA, showing certain overlapping recombinable units (A) and resulting alleles that are generated by the action of a first recombinase (B) or a second (C) and third (D) recombinase.

In a specific embodiment, the MFA comprises a placement of recombinase sites and COIN, NSI, DSC, and reporter as shown in FIG. 12, Panel A. Treatment with a selected recombinase results in the allele shown in FIG. 12, Panel B. Alternate treatment with a different selected recombinase results in the allele shown in FIG. 12, Panel C. Treatment of the allele of FIG. 12, Panel C with yet another different recombinase results in the allele shown in FIG. 12, Panel D.

In one aspect, a nucleic acid construct is provided, comprising a MFA comprising, from 5' to 3' with respect to the direction of transcription, a reporter in sense orientation, a DSC, an NSI in antisense orientation, and a COIN in antisense orientation; whereupon treatment of the MFA with a first selected recombinase, the reporter is excised, the NSI is placed in sense orientation, and the COIN remains in antisense orientation, and wherein the allele comprises recombinase sites that allow for an inversion of sequence that upon treatment with a second selected recombinase would place the COIN in sense orientation and the NSI in antisense orientation. In one embodiment, following with the first selected recombinase, the allele is treated with the second selected recombinase. In one embodiment, the COIN signals that the NSI has been placed in antisense orientation following treatment with the second recombinase.

In one embodiment, the MFA comprises, from 5' to 3' with respect to the direction of transcription, a recombinase site R1, a reporter, a second recombinase site R2, a DSC, a third recombinase site R3, an NSI in antisense orientation, a fourth recombinase site R4, a fifth recombinase site R5, a sixth recombinase site R1' that is compatible with R1 and that is oriented with respect to R1 to direct an inversion, a seventh recombinase site R3' that is compatible with R3 and that is oriented with respect to R3 to direct an inversion, a COIN in antisense orientation, an eighth recombinase site R5' that is compatible with R5 and that is oriented with respect to R5 to direct an excision, a ninth recombinase site R4' that is compatible with R4 and that is oriented with respect to R4 to direct an excision, and a tenth recombinase site R2' that is compatible with R2 and that is oriented with respect to R2 to direct an excision. In a specific embodiment, R1/R1' are FRT3 or FRT sites, R2/R2' are Rox sites, R3/R3' are FRT3 or FRT sites that are different from R1/R1', R4/R4' are loxP or lox2372 sites, and R5/R5' are loxP or lox2372 sites that are different from R4/R4' sites.

Figure 13:
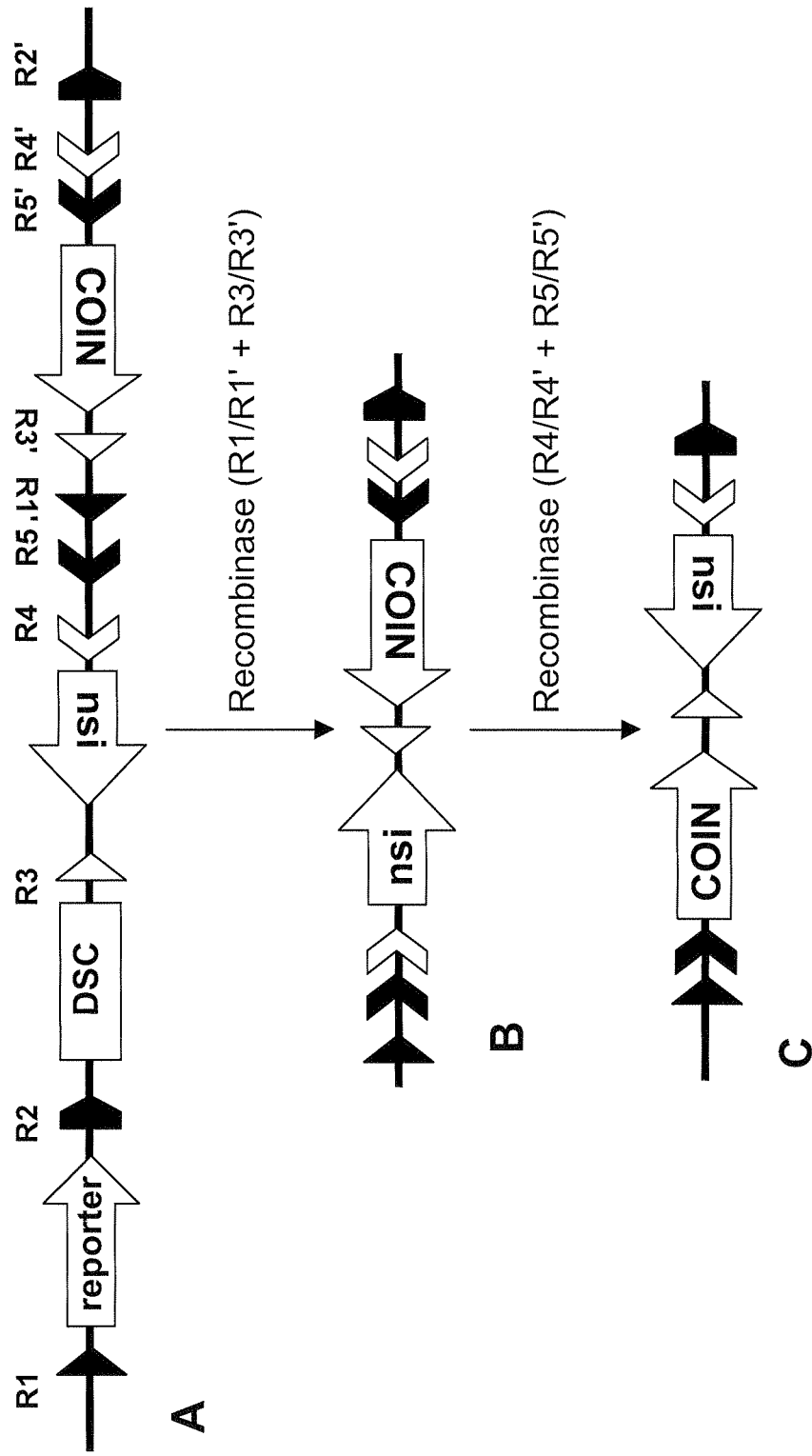
FIG. 13 illustrates an embodiment of an MFA (A), showing resulting alleles that result from action of a first recombinase that places the NSI in sense orientation (B) and a second recombinase that places the NSI in antisense orientation while placing the COIN in sense orientation (C).

In a specific embodiment, the MFA comprises a placement of recombinase sites and COIN, NSI, DSC, and reporter as shown in FIG. 13, Panel A. Treatment with a selected recombinase results in the allele shown in FIG. 13, Panel B. Treatment of the allele of FIG. 13, Panel B with a different recombinase results in the allele shown in FIG. 13, Panel C.

In one aspect, a nucleic acid construct is provided, comprising a MFA comprising, from 5' to 3' with respect to the direction of transcription, a COIN in antisense orientation, an NSI in antisense orientation, a DSC, and a reporter in sense orientation; whereupon treatment of the MFA with a first selected recombinase, the reporter is excised, the NSI is placed in sense orientation, and the COIN remains in antisense orientation, and wherein the allele comprises recombinase sites that allow for an inversion of sequence that upon treatment with a second selected recombinase would place the COIN in sense orientation and the NSI in antisense orientation. In one embodiment, following with the first selected recombinase, the allele is treated with the second selected recombinase. In one embodiment, the COIN signals that the NSI has been placed in antisense orientation following treatment with the second recombinase.

In one embodiment, the MFA comprises, from 5' to 3' with respect to the direction of transcription, a recombinase site R1, a second recombinase site R2, a third recombinase site R3, a COIN in antisense orientation, a fourth recombinase site R4, a fifth recombinase site R5, a sixth recombinase site R3' that is compatible with R3 and that is oriented with respect to R3 to direct an excision, a seventh recombinase site R2' that is compatible with R2 and that is oriented with respect to R2 to direct an excision, an NSI in antisense orientation, an eighth recombinase site R4' that is compatible with R4 and that is oriented with respect to R4 to direct an inversion, a DSC, a ninth recombinase site R1' that is compatible with R1 and that is oriented with respect to R1 to direct an excision, a reporter in sense orientation, and a tenth recombinase site R5' that is compatible with R5 and that is oriented with respect to R5 to direct an inversion. In a specific embodiment, R1/R1' are Rox sites sites, R2/R2' are loxP or lox2372 sites, R3/R3' are loxP or lox2372 sites that are different from R2/R2', R4/R4' are FRT or FRT3 sites, and R5/R5' are FRT or FRT3 sites that are different from R4/R4'.

Figure 14:
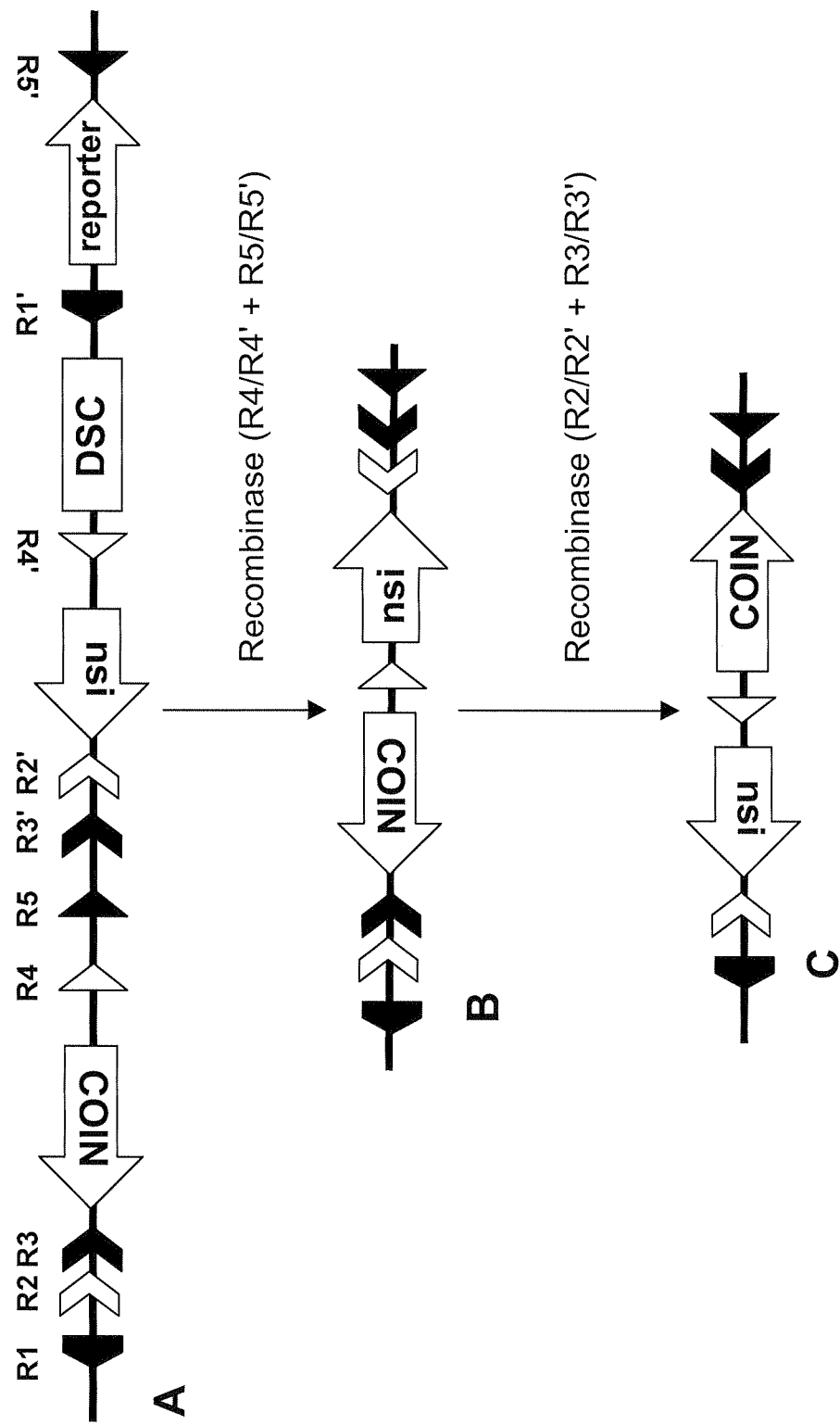
FIG. 14 illustrates an embodiment of an MFA (A), showing resulting alleles that result from action of a first recombinase that places the NSI in sense orientation (B) and a second recombinase that places the NSI in antisense orientation while placing the COIN in sense orientation (C).

In a specific embodiment, the MFA comprises a placement of recombinase sites and COIN, NSI, DSC, and reporter as shown in FIG. 14, Panel A. Treatment with a selected recombinase results in the allele shown in FIG. 14, Panel B. Treatment of the allele of FIG. 14, Panel B with a different recombinase results in the allele shown in FIG. 14, Panel C.

In one aspect, a nucleic acid construct is provided, comprising a MFA comprising, from 5' to 3' with respect to the direction of transcription, an NSI in antisense orientation, a DSC, a reporter in sense orientation, and a COIN in antisense orientation; whereupon treatment of the MFA with a first selected recombinase, the reporter is excised, the DSC is excised, the NSI is placed in sense orientation, and the COIN remains in antisense orientation, and wherein following treatment with the first selected recombinase the allele comprises recombinase sites that allow for an inversion of sequence that upon treatment with a second selected recombinase would place the COIN in sense orientation and the NSI in antisense orientation. In one embodiment, following with the first selected recombinase, the allele is treated with the second selected recombinase. In one embodiment, the COIN signals that the NSI has been placed in antisense orientation following treatment with the second recombinase.

In one embodiment, the MFA comprises, from 5' to 3' with respect to the direction of transcription, a recombinase site R1, a second recombinase site R2, a third recombinase site R3, an NSI in antisense orientation, a fourth recombinase site R4, a fifth recombinase site R5, a sixth recombinase site R2' that is compatible with R2 and that is oriented with respect to R2 to direct an inversion, a DSC, a seventh recombinase site R1' that is compatible with R1 and that is oriented with respect to R1 to direct an excision, a reporter in sense orientation, an eighth recombinase site R3' that is compatible with R3 and that is oriented with respect to R3 to direct an inversion, a COIN in reverse orientation, a ninth recombinase site R5' that is compatible with R5 and that is oriented with respect to R5 to direct an excision, and a tenth recombinase site R4' that is compatible with R4 and that is oriented with respect to R4 to direct an excision. In a specific embodiment, R1/R1' are Rox sites, R2/R2' are FRT or FRT3 sites, R3/R3' are FRT or FRT3 sites that are different from R2/R2', R4/R4' are loxP or lox2372 sites, and R5/R5' are loxP or lox2372 sites that are different from R4/R4'.

Figure 15:
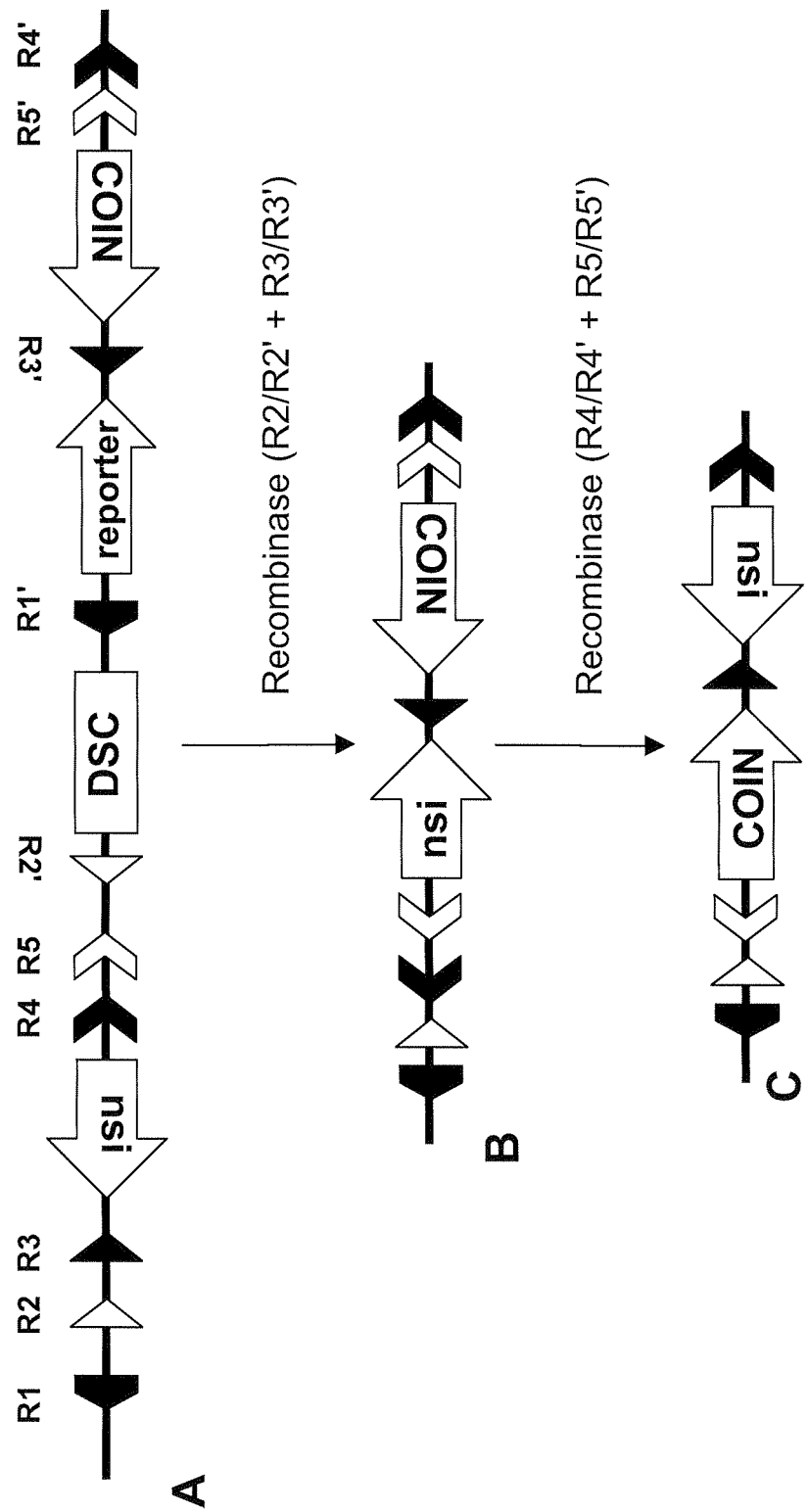
FIG. 15 illustrates another embodiment of an MFA (A), showing resulting alleles that result from action of a first recombinase that places the NSI in sense orientation (B) and a second recombinase that places the NSI in antisense orientation while placing the COIN in sense orientation (C).

In a specific embodiment, the MFA comprises a placement of recombinase sites and COIN, NSI, DSC, and reporter as shown in FIG. 15, Panel A. Treatment with a selected recombinase results in the allele shown in FIG. 15, Panel B. Treatment of the allele of FIG. 15, Panel B with a different recombinase results in the allele shown in FIG. 15, Panel C.

In one aspect, a multifunctional allele is provided, comprising a DSC, a reporter, a COIN, a NSI, and five pairs of recombinase sites arranged among the reporter, the DSC, the COIN, and the NSI, wherein no pair of recombinase sites is identical to any other pair, and wherein a first two pairs of recombinase sites are recognized by the same first recombinase, a second two pairs of recombinase sites are recognized by the same second recombinase, and the fifth pair of recombinase sites are recognized by a third recombinase, wherein the first, second, and third recombinases are not identical, and wherein, with respect to direction of transcription, the MFA comprises (from 5' to 3'): (a) an actuating sequence (e.g., with reporter) in sense orientation, the DSC in sense or antisense orientation, the NSI in antisense orientation, the COIN in antisense orientation; (b) the COIN in antisense orientation, the NSI in antisense orientation, the DSC in sense or antisense orientation, the reporter in sense orientation; (c) the NSI in antisense orientation, the DSC in sense or antisense orientation, the reporter in sense orientation, the COIN in antisense orientation; (d) the reporter in sense orientation, the DSC in sense or antisense orientation, the NSI in antisense orientation, the COIN in antisense orientation; (e) the COIN is in antisense orientation, the NSI in antisense orientation, the DSC in sense or antisense orientation, the reporter in sense orientation; or, (f) the NSI in antisense orientation, the DSC in sense or antisense orientation, the reporter in sense orientation, the COIN in antisense orientation.

In one embodiment, the arrangement is as in (a), and the pairs of recombinase sites are arranged such that upon exposure to the third recombinase, the fifth pair of recombinase sites direct an excision of the DSC, the NSI, and the COIN, wherein the reporter is maintained in sense orientation.

In one embodiment, the arrangement is as in (a), and the pairs of recombinase sites are arranged such that upon exposure to the first recombinase, a modified MFA forms wherein the first two pairs of recombinase sites direct excision of the reporter and excision of the DSC and inversion of the NSI to sense orientation, wherein the COIN is maintained in antisense orientation. In a further embodiment, the modified MFA comprises the second two pairs of recombinase sites that, upon exposure to the second recombinase, result in an allele wherein the NSI is excised and the COIN is placed in sense orientation.

In one embodiment, the arrangement is as in (b), and the pairs of recombinase sites are arranged such that upon exposure to the third recombinase, the fifth pair of recombinase sites direct an excision of the COIN, the NSI, and the DSC, wherein the reporter is maintained in sense orientation.

In one embodiment, the arrangement is as in (b), and the pairs of recombinase sites are arranged such that upon exposure to the first recombinase, a modified MFA forms wherein the first two pairs of recombinase sites direct excision of the DSC and the reporter and direct inversion of the NSI to the sense orientation, wherein the COIN is maintained in antisense orientation. In a further embodiment, the modified MFA comprises the second two pairs of recombinase sites that, upon exposure to the second recombinase, result in an allele wherein the NSI is excised and the COIN is placed in sense orientation.

In one embodiment, the arrangement is as in (c), and the pairs of recombinase sites are arranged such that upon exposure to the third recombinase, the NSI and the DSC are excised and the reporter and the COIN are maintained in antisense orientation.

In one embodiment, the arrangement is as in (c), and the pairs or recombinase sites are arranged such that upon exposure to the first recombinase, a modified MFA forms wherein the DSC and the reporter are excised, and the NSI is placed in sense orientation, wherein the COIN is maintained in antisense orientation. In a further embodiment, the modified MFA comprises the second two pairs of recombinase sites that, upon exposure to the second recombinase, result in an allele wherein the NSI is excised and the COIN is placed in sense orientation.

In one embodiment, the arrangement is as in (d), and the pairs of recombinase sites are arranged such that upon exposure to the third recombinase, the DSC, the NSI, and the COIN are excised and the reporter is maintained in sense orientation.

In one embodiment, the arrangement is as in (d), and the pairs of recombinase sites are arranged such that upon exposure to the first recombinase, a modified MFA forms wherein the reporter and the DSC are excised, and the NSI is placed in sense orientation, wherein the COIN is maintained in antisense orientation. In a further embodiment, the modified MFA comprises the second two pairs of recombinase sites that, upon exposure to the second recombinase, result in an allele wherein the COIN is placed in sense orientation and the NSI is placed in antisense orientation.

In one embodiment, the arrangement is as in (e), and the pairs of recombinase sites are arranged such that upon exposure to the third recombinase, the COIN, the NSI, and the DSC are excised and the reporter is maintained in sense orientation.

In one embodiment, the arrangement is as in (e), and the pairs of recombinase sites are arranged such that upon exposure to the first recombinase, a modified MFA is formed wherein the DSC and the reporter are excised, the NSI is placed in sense orientation, and the COIN is maintained in antisense orientation. In a further embodiment, the modified MFA comprises the second two pairs of recombinase sites arranged such that, upon exposure to the second recombinase, the NSI is placed in antisense orientation and the COIN is placed in sense orientation.

In one embodiment, the arrangement is as in (f), and the pairs of recombinase sites are arranged such that upon exposure to the third recombinase, the NSI and the DSC are excised, the reporter is maintained in sense orientation, and the COIN is maintained in antisense orientation.

In one embodiment, the arrangement is as in (f), and the pairs of recombinase sites are arranged such that upon exposure to the fifth recombinase, the NSI and the DSC are excised and the reporter is maintained in sense orientation and the COIN is maintained in antisense orientation.

In one embodiment, the arrangement is as in (f), and the pairs of recombinase sites are arranged such that upon exposure to the first recombinase, a modified MFA is formed wherein the DSC and the reporter are excised and the NSI is placed in sense orientation and the COIN is maintained in antisense orientation. In a further embodiment, the modified MFA comprises the second two pairs of recombinase sites arranged such that, upon exposure to the second recombinase, the NSI is placed in antisense orientation and the COIN is placed in sense orientation.

In one aspect, a method for making a cell that comprises a construct having a nucleotide sequence of interest in antisense orientation and a COIN in antisense orientation is provided, comprising the step of introducing into a genome of a cell an MFA as described herein, identifying the cell comprising the MFA, followed by a step of exposing the genome to a first recombinase, wherein action of the first recombinase on the construct in the genome results in the nucleotide sequence of interest being placed in the sense orientation.

In one embodiment, the cell is a pluripotent cell, an induced pluripotent cell, a totipotent cell, or an ES cell. In a specific embodiment, the ES cell is a mouse or rat ES cell.

In one embodiment, the construct is introduced into the cell by homologous recombination. In another embodiment, the construct is randomly integrated into a nucleic acid of the cell. In one embodiment, the nucleic acid of the cell is the cell's genome.

In one embodiment, the NSI comprises an exon. In one embodiment, the NSI comprises an exon and flanking intronic sequence. In a specific embodiment, the flanking exon is flanked 5' and 3' with intronic sequence. In one embodiment, the nucleotide sequence comprises two or more exons, and in a specific embodiment comprises intronic sequence(s). In another embodiment, the NSI lacks an exon, or lacks a fragment of an exon.

In one embodiment, the NSI is a wild-type exon or exons of a gene. In another embodiment, the NSI is an exon or exons of a gene having one or more nucleic acid substitutions, deletions, or additions.

In one embodiment, the COIN comprises an exon of a gene that comprises one or more nucleic acid substitutions, deletions, or additions. In a specific embodiment, the COIN comprises an exon of a human, mouse, monkey, or rat gene.

In one embodiment, the COIN comprises a 3' splice region. In a specific embodiment, the 3' splice region is followed by a sequence selected from a cDNA, an exon-intron sequence, a microRNA, a microRNA cluster, a small RNA, a codon-skipping element, an IRES, a polyadenylation sequence, and a combination thereof. In a specific embodiment, the small RNA is a mirtron. In a specific embodiment, the codon-skipping element is T2A, E2A, or F2A.

In one embodiment, the COIN is selected from a reporter, a gene trap-like element (GT-like element), and a gene trap-like reporter (GT-like reporter). In a specific embodiment, the GT-like element is selected from SA-drug resistance cDNA-polyA. In a specific embodiment, the GT-like reporter is selected from SA-reporter-polyA.

In one aspect, a method is provided for placing a multifunctional allele in a mouse cell genome, comprising a step of introducing into a locus in a mouse cell a targeting construct comprising a first recombinable unit that comprises (a) an actuating sequence (e.g., a nucleotide sequence and/or a reporter); (b) a DSC; (c) a NSI in antisense orientation with respect to the locus; (d) a COIN in antisense orientation with respect to the locus; and, (e) site-specific recombinase recognition sites arranged in recombinable units for deleting the reporter and the DSC, for inverting the NSI back to the sense orientation, and for inverting the COIN and deleting or re-inverting the NSI.

In one embodiment, the site-specific recombinase recognition sites are arranged in recombinable units such that the NSI will be re-inverted into the antisense strand and the COIN will be inverted into the sense strand. In another embodiment, the site-specific recombinase recognition sites are arranged in recombinable units such that the NSI will be deleted and the COIN will be inverted into the sense strand.

In one embodiment, the recombinable units are arranged such that upon exposure of the MFA-modified target locus to a first recombinase, a first recombinable unit comprising the reporter and DSC are deleted and the NSI is placed in the sense orientation with respect to the locus and the COIN is maintained in the antisense orientation, forming a second recombinable unit.

In one embodiment, the nucleotide sequence of interest in antisense orientation is an exon in the antisense orientation, or an exon flanked by intronic sequence wherein the exon and the intronic sequence are each in antisense orientation. In a specific embodiment, the exon being placed in the antisense orientation is identical to the exon being replaced by the targeting construct. In a specific embodiment, the NSI in antisense orientation is an exon and sequence surrounding the exon. In a specific embodiment, the NSI is two or more exons. In a specific embodiment, the NSI is non-exonic sequence.

In one embodiment, the second recombinable unit generated by the action of the first recombinase is exposed to a second recombinase, wherein the second recombinase deletes the NSI and places the COIN in the sense orientation.

In one embodiment, the second recombinable unit generated by the action of the first recombinase is exposed to a second recombinase, wherein the second recombinase places the NSI in antisense orientation and places the COIN in sense orientation.

In one aspect, a method for complementation of a knockout is provided, comprising introducing into a nonhuman animal an MFA as described herein, wherein the nucleic acid construct comprises a wild-type nucleic acid sequence in antisense orientation and a COIN in the antisense orientation, wherein upon exposure of the nucleic acid construct to a first recombinase the wild-type nucleic acid sequence inverts to sense orientation and is transcribed but the COIN remains in the antisense orientation; and wherein upon exposure to a second recombinase the wild type nucleic acid sequence is excised, or inverted back to the antisense strand, and the COIN inverts to sense orientation.

In one embodiment, the nonhuman animal is a mouse.

In one embodiment, the COIN is a reporter element. In one embodiment the reporter element is selected from a fluorescent protein, a luminescent protein, or an enzyme. In a specific embodiment, the reporter is selected from GFP, eGFP, CFP, YFP, eYFP, BFP, eBFP, DsRed, MmGFP, luciferase, LacZ, and Alkaline Phosphatase.

In one aspect, a mammalian cell comprising a multifunctional allele in accordance with the invention is provided.

In one embodiment, the mammalian cell is selected from a mouse cell, and a rat cell. In one embodiment, the cell is selected from a stem cell, an embryonic stem (ES) cell, an induced pluripotent cell, a pluripotent cell, and a totipotent cell.

In one aspect, a non-human embryo or non-human animal comprising a multifunctional allele in accordance with the invention is provided.

In one embodiment, the non-human embryo or non-human animal comprises a multifunctional allele that has been exposed to one or more site-specific recombinases. In a specific embodiment, the multifunctional allele has been exposed to the one or more site-specific recombinases as the result of a breeding step wherein a non-human animal comprising a multifunctional allele has been mated with a non-human animal comprising the one or more site specific recombinases, and the non-human embryo or non-human animal is a progeny of the breeding step.

In one aspect, a cell comprising an MFA as described herein is provided, wherein the cell is a mammalian cell, e.g., an ES cell or pluripotent or induced pluripotent cell. In a specific embodiment, the cell is a mouse or rat cell.

In one aspect, a non-human animal is provided, comprising an MFA as described herein, or an MFA that has been exposed to one or more recombinases as described herein.

In one aspect, a non-human embryo is provided, comprising an MFA as described herein, or an MFA that has been exposed to one or more recombinases as described herein.

In one aspect, a cell, a non-human embryo, or a non-human animal made using an MFA as described herein is provided.

In one aspect, a cell, a non-human embryo, or a non-human animal made using an MFA as described herein is provided.

Any aspect or embodiment can be used in connection with any other aspect or embodiment as appropriate, e.g., any reporter or DSC recited in connection with any particular MFA embodiment can be used with any MFA embodiment described herein, and any particular recombinase or recombinase site mentioned in connection with any particular MFA embodiment can be used with any MFA embodiment described herein.

Other embodiments are described and will become apparent to those skilled in the art from a review of the ensuing detailed description.

DETAILED DESCRIPTION

The invention is not limited to particular methods, and experimental conditions described, as such methods and conditions may vary. The terminology used herein is for the purpose of describing particular embodiments only, and is not intended to be limiting, since the scope of the present invention will be limited only by the claims.

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, particular methods and materials are now described. All publications mentioned herein are incorporated herein by reference in their entirety.

The phrase "sense orientation," or "sense," refers to the coding direction or sense strand of a transcribable nucleic acid sequence in the local context of the genome, e.g., when a sequence is placed in "sense orientation" in or near a transcribable sequence in a genome, the orientation of the sequence is compatible with transcription and, for protein-coding genes also translation of the sequence in the region or locus or gene in which the sequence is placed. The phrase "antisense orientation," or "antisense," refers to placement of a sequence at a region or locus or gene in which the sequence is in the strand opposite (or antisense) to that which is compatible with transcription. Thus, in a specific example, if a sequence is placed in "sense" orientation in a gene, it can generally be transcribed. If a sequence is placed in "antisense" orientation, it generally will not be transcribed. For loci where transfer between sense and antisense strands might result in transcription from either strand, the sequence can be selected or engineered such that transfer from sense to antisense or from antisense to sense would result in transcription from one strand, but not either.

The term "COIN" includes reference to a conditional element. A conditional element comprises a nucleotide sequence whose expression (or failure to express) is contingent upon the occurrence of an independent event. For example, a coding region that in a sense orientation would either encode a protein or fragment thereof or a non-coding RNA (ncRNA) is placed in antisense orientation flanked on both sides by site-specific recombination sites in opposite orientation. In the absence of a site-specific recombinase that recognizes the flanking sites, the coding region is not transcribed, because it is placed in the antisense strand with respect to the target gene. Upon treatment with the cognate site-specific recombinase, the COIN sequence is inverted, and as a result it becomes incorporated into the transcribed message, resulting in expression of the protein or fragment thereof or in the of the ncRNA.

The term "incompatible," when used to describe two or more recombinase recognition sites, refers to the quality that the two or more recombinase recognition sites cannot be recombined with one another (but the two or more recombinase recognition sites can be recombined with other cognate (e.g., identical) recombinase recognition sites).

Knockouts and Conditional Alleles

The study of gene function by genetic methods has relied on the discovery of naturally occurring variants or mutant alleles, or on the deliberate generation of such variants and mutant alleles. The latter has proceeded either by the random mutagenesis followed by phenotype-based screens and then elucidation of the causative mutation—a process that has been referred to as "forward genetics", or by genetic engineering methodology whereby mutations are rendered in specific "target" genes or loci—an approach that has been referred to as "reverse genetics."

In the mouse—the most widely used mammalian model organism—the ability to engineer specific, molecularly extremely well defined mutations via gene targeting has dominated the field of reverse genetics. However, the majority of variants made to date have been relatively simple null alleles, commonly referred to as "knockout alleles" or simply "knockouts", and usually encompass a deletion of the exon-intron region of a gene or part thereof, and in more recent years with concomitant replacement of that region with a reporter cDNA, such as LacZ. The adaptation of site-specific recombinases and their cognate recognition sites (such as Cre/lox, Dre/Rox, PhiC31\int/attP-attB, Flp/FRT), derived from bacteriophages or yeast and modified for use in mammalian cells, is a more recent development that has not only made possible the post-targeting excision of the DSC (as long as it is flanked by site-specific recombinase recognition sites) but has also enabled the engineering of conditional-null alleles. Conditional-null alleles have been developed wherein the exon-intron region of the target gene—or more frequently a part thereof—is flanked by recombinase recognition sites, rendering the modified allele amenable to conversion to the null state by the action of the cognate recombinase. The advantage of this method over regular knockouts is that the conversion of the modified gene to a knockout can be spatio-temporally controlled by controlling the place (organ, tissue, or cell type), time, and sometimes, also the duration that the cognate recombinase will be active.

Traditionally, conditional-null alleles have been engineered as a follow-up to the corresponding simple knockout alleles, mostly in cases where the latter is either embryonic lethal and/or displays a plurality of phenotypes, hence rendering the study of the target gene's function impossible in an adult setting (in the case of embryonic lethality), or hard to interpret in a specific cell type or biological process (in the case where the gene displays a plurality of phenotypes). Given the amount of effort, time, and expense that it takes to generate genetically modified mice via gene-targeting, this step-wise fashion of first generating a knockout, then deciphering its phenotype, and then engineering a conditional-null, has been considered burdensome by an increasing number of investigators. In addition, for a small number of genes, regular knockout alleles cannot go through the germline as they result in embryonic lethality even at the heterozygous null state. Therefore, the desire to be able to engineer dual (null and conditional) or even multi-modality alleles in a single gene-targeting step has been a persistent goal of those involved in the art as well as the community of end users. Two methods have indeed tried to address this need: FlEx and Knockout-first (KO-first).

The FlEx method has been used both for targeting and as a gene trap (GT), but the basic design principles are the same irrespective of the final application. A basic design of a FlEx is shown in FIG. 1, with U representing, e.g., a DSC and D representing a reporter. The result of recombinase action on the FlEx construct is permanent deletion of the U element (e.g, the DSC) and inversion (and expression) of the D element (e.g., the reporter).

In its original embodiment and application, FlEx was developed as a method to engineer conditional alleles. FlEx was first used to generate a "conditional-null" allele for Rarg, by inserting the FlEx cassette into this gene such that a loxP/lox511 couplet was inserted upstream of exon 8 of Rarg, and the remainder of the FlEx cassette—composed 5' to 3' of SA-lacZ-SV40polyA (a GT-like element) in the antisense orientation with respect to Rarg, and then another loxP/lox511 couplet in the antisense orientation with respect to the firstloxP/lox511 couplet, and containing a neomycin phosphotransferase mini gene (neo) in the sense orientation—into intron 8 of Rarg. This design empowers Cre-mediated inversion of the GT-like element SA-lacZ-SV40polyA such that it is brought into the sense strand and acts as a gene trap; simultaneously, exon 8 of Rarg is brought into the antisense orientation (effectively ensuring that even in the case where transcription does not terminate at the end of the GT-like element SA-lacZ-SV40polyA, exon 8 will not be incorporated into the read-through message), while neo is simultaneously deleted, and thereby resulting in a null allele of Rarg in which the expression of Rarg is replaced by that of lacZ.

However, in spite of the success of this method in generating a null allele (by exposure to Cre), the unrearranged (pre-Cre) FlEx allele of Rarg was not a true conditional-null, as originally designed, but rather a severe hypomorphic allele, where the expression of $Rarg^{FLEx}$ was significantly reduced in comparison to Rarg. As a result, $Rarg^{FLEx/FLEx}$ mice displayed a phenotype that resembled a less severe form of the Rarg knockout mice, and revealing the inability of this initial embodiment of FlEx to generate a true conditional-null allele.

The FlEx method has been also adapted for use in gene trapping. In that variation of the method, a GT element (SA-βgeo-polyA, where βgeo is an in-frame fusion of lacZ with neo open reading frames, hence combining the ability to report via LacZ and select via Neo) was flanked by FlEx-like arrays, an outer array composed of an FRT/FRT3 couplet, and an inner array composed of an loxP/lox511 couplet, both in mirror image configuration with respect to one another. In this manner, successful incorporation of the resulting GT vector into actively transcribed genes would result in expression of βgeo and hence allow selection for these events by selecting for G418, and depending on the site of incorporation of the GT element theoretically also result in the generation of functional null alleles for the corresponding genes. Once a gene has been trapped to generate the corresponding FIEx allele, the resulting allele may be a knockout allele or a hypomorphic allele, i.e., one where the expression of the trapped gene is downregulated. Treatment of these FIEx alleles with Flp recombinase should in principle invert the GT element to the anti-sense strand, thereby alleviating transcriptional termination within the trap element, and hence converting the modified gene to conditional GT. This conditional GT, now "hidden" in the antisense strand, can be reactivated by exposure to Cre, which will re-invert it by acting on the loxP/lox511 couplets of the FIEx array.

This application of FIEx technology relies on a GT element to generate null alleles. It is therefore subject to the limitations of gene trapping technology, which does not guarantee that a true knockout will be generated and takes on the additional risk of inactivating regulatory elements (by random insertional inactivation). Both the placement of the GT element as well as the degree that it is effective in terminating transcription can impact whether any given allele will be a null allele. An additional problem is that for the majority of genes that do not have an already established function, and more so one that links the gene to a phenotype determined through the study of a definitive null allele, it is very difficult to prove conclusively that a GT allele is truly a null allele. In fact, for these as well as other, mostly technical reasons, after 4 years of adoption and use by a large scale mouse mutagenesis consortium—EUCOMM— the FIEX-based gene trapping method has been abandoned in favor of gene targeting using the KO-first method.

Similar to the FIEx method, typical current KO-first alleles rely at least in part on a GT-like element (either SA-LacZ-polyA or SA-βgeo-polyA) to generate a knockout-like allele. However, in recognition of the limitations that have been associated with that approach (effectively learning from the experience gained with GTs, as well as theoretical considerations), KO-first also requires that the floxed critical exon downstream of the GT-like element must be deleted (using Cre) in order to generate a true null allele. Therefore, in practice, this method first requires placement of a FRT-flanked reporter/GT-like cassette plus a drug minigene into an intron of the target gene somewhere upstream of the exon to be deleted, while simultaneously floxing the exon slated to be deleted. This exon has been referred to as the "critical exon", and irrespective of the criteria that are used to define "critical exon", the KO-first method clearly requires its removal in order to render the resulting allele a true null. Therefore, following targeting, the resulting allele is neither a true null nor a conditional-null allele. The reasons that the resulting allele is not a true null has been attributed to the fact that without removal of the critical exon (which is floxed) by Cre, there remains the possibility of read-through transcription and splicing around of the GT-like cassette, as well as transcription of the gene's message downstream of the GT-like cassette due to the presence of the drug mini-gene. The reason that the resulting allele is not a conditional-null allele lies in the fact that without removal of both the reporter/GT-like cassette and the drug mini-gene, generation of the normal message (normal composition, as well as level and sites of expression) cannot take place.

Therefore, depending on the desired use—null or conditional-null—KO-first alleles must be subjected to a second post-targeting step. In the case where a true null is desired, the KO-first allele must be treated with Cre recombinase to delete the critical exon (which is floxed).

Conversely, a conditional allele can be generated after a Flp-mediated removal of the reporter/GT-like cassette and the drug mini-gene, which are together flanked by FRT sites. In this manner, the only modifications that remain are an FRT site and the floxed "critical" exon. This allele in turn can be converted to null by Cre-mediated removal of the floxed exon.

Although the KO-first method addresses some of the limitations of FIEx, it is still hampered by three main drawbacks that limit its utility: first, although it rectifies the lack of reliability of GT-like elements to generate a true KO-first, it fails to provide a true KO-first without an additional post-targeting step; second, due to the criteria used to define "critical exons", KO-first is limited to protein-coding genes, effectively placing out of reach all the non-protein coding genes (i.e., those that encode 'non-coding' RNAs, a class of the very important biomolecules). Furthermore, of the protein-coding genes only those for which a "critical exon" can be defined are amenable to the KO-first design. The criteria for defining a critical exon are that its deletion results in a frame shift between the part of the open reading frame (ORF) preceding it and the part of the ORF following it. This is because induction of this frame shift is obligatory for the KO-first method to provide a definitive knockout. Therefore, even certain classes of protein-coding genes are not amenable to KO-first design. These include genes where the ORF is contained within one exon, and genes where all or the majority of tandem exons leave off in the same frame. Thirdly, once the KO-first allele has been converted into a conditional-null allele (by the action of Flp), the resulting allele does not provide any mechanism for affirmative reporting of nullness upon conversion of the conditional allele to the null state. Typically, knockout-first alleles remove the reporter (e.g., lacZ) together with the DSC using (a step accomplished using Flp recombinase, as the SA-lacZ-polyA and DSC used in KO-first are FRTed) leaving behind only the floxed exon (plus a FRT site upstream of it). Thus, no option exists in conventional knockout-first approaches for a reporter function to report achievement of a null allele.

Multifunctional Alleles

A multifunctional allele (MFA) approach is provided that permits removal or inactivation of a nucleotide sequence in a genome by introduction of a set of functional elements that comprise an actuating sequence (which confirms removal or inactivation), resulting in a true knockout, and that also contains one or more conditional elements whose expression in the allele is conditional (i.e., dependent on certain molecular events or cues) and reportable.

The MFA approach provides targeting options to generate true knockout-first alleles that do not require a second post-targeting step to convert the targeted alleles to null status, thus providing an advantage and conceptual breakthrough over typical current knockout-first alleles that require a post-targeting step to convert targeted alleles to null alleles. The MFA approach is also not limited to use with "critical exons" and not limited to knockouts by frameshifts, but is generally applicable for modifying any nucleotide sequence of interest. MFAs provide enhanced versatility and a multiplicity of allele options following a single targeting step.

The MFA approach provides a true KO-first allele that provides the opportunity for creating a second state in the recipient genome upon inversion of any selected sequence linked with an actuating sequence, and wherein upon inversion transcription of the selected sequence can be reported. The selected sequence can be, e.g., a COIN, which, without limitation, can itself comprise an actuating sequence that, e.g., comprises a repressor to control transcription of another gene or regulatory sequence. In one example, a single targeting step placing an MFA at a locus can allow modification of a wild-type locus to a particular state, State A (e.g., a knockout of an endogenous gene). The MFA is designed to enable a change of state to another particular state, State B (e.g., reinstatement of a wild-type phenotype), through the action of a first recombinase. State B can be converted to State C (e.g., reestablishment of the knockout and expression of a COIN) by a second recombinase, and so on. Thus, varying states at a selected locus can be achieved from a single initial allele when employing MFAs.

The MFA approach can be used to place an MFA as a gene trap, such that the transgene comprising the MFA obtains expression of MFA elements employing an endogenous transcriptionally active promoter.

The MFA approach can be used in traditional transgenesis applications wherein the actuating sequence comprises a promoter, exon, or exons and introns, and optionally transcriptional control elements and followed by a DSC (optional, as it is not necessary for traditional, pronuclear-injection based transgenesis), an NSI (that can be a second actuating sequence) in the antisense orientation with respect to the first actuating sequence, and a COIN (that can be a third actuating sequence) also placed in the antisense orientation with respect to the first actuating sequence.

The MFA approach provides a multiplicity of options for creating loci that contain null alleles, conditional null alleles, COINs, actuating sequences (which can include reporters) and DSCs, and other elements, in a single targeting step. Post-targeting manipulations of the locus provide options through the use of recombinable units introduced into the MFA-containing locus with the MFA construct in the single targeting step. The number of different recombinases required to exercise the various manipulable options at the locus post-targeting is reduced by employing different pairs of cognate site-specific recombinase recognition sites that are incompatible (e.g., a pair of FRT sites and a pair of FRT3 sites, a pair of loxP sites and a pair of lox2372 sites, etc.). Thus, exposure of an MFA-containing locus to a single recombinase can independently act on at least two different recombinable units, to recombine a unit such that the unit places elements of interest (e.g., reporters, DSCs, exons, COINs, etc.) in desired orientations, as well as re-orienting site-specific recombinase recognition sites within the recombinable unit to form new recombinable units.

The MFA approach provides an option for a COIN that can contain any desired sequence, including but not limited to a reporter, or a cDNA encoding a mutant or variant form of the target gene or part of the target gene, or relatives and homologs of the target gene, or even non-protein coding sequences such as microRNAs or clusters of microRNAs, or any combinations of these elements (as they can be accommodated by the placement of internal ribosome entry sites or "self-cleaving" peptides—depending on the choice of elements—between the different elements).

The MFA approach provides an option wherein knockout is achieved by targeting, a first recombinase is employed to reestablish the knocked out element back into an active (wild type) state, and a second recombinase is employed to reestablish the knockout, wherein a COIN is placed in sense orientation concomitant with reestablishment or knock-in of the knocked out element, thus reporting the reestablishment of the knockout in the cells where the second recombinase has been activated.

Figure 5:
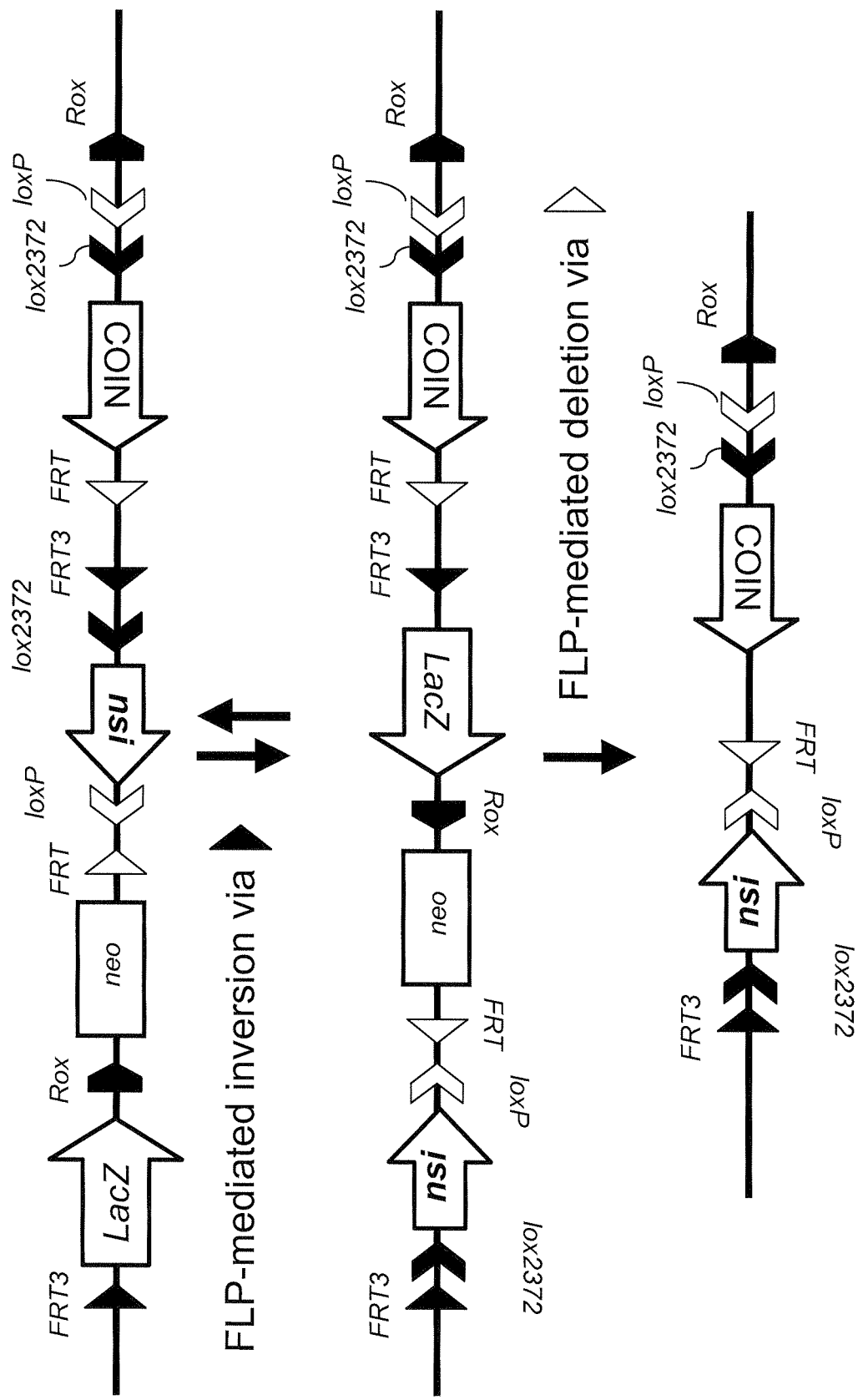
FIG. 5 illustrates a particular embodiment of an MFA that generates a conditional allele that contains/incorporates a COIN from an MFA using a single recombinase (here, a Flp recombinase first acting on FRT3 sites of the allele embodiment). For simplicity, the splice acceptor and splice region preceding the LacZ sequence, and the polyA signal following the LacZ sequence, are not shown.
Figure 6:
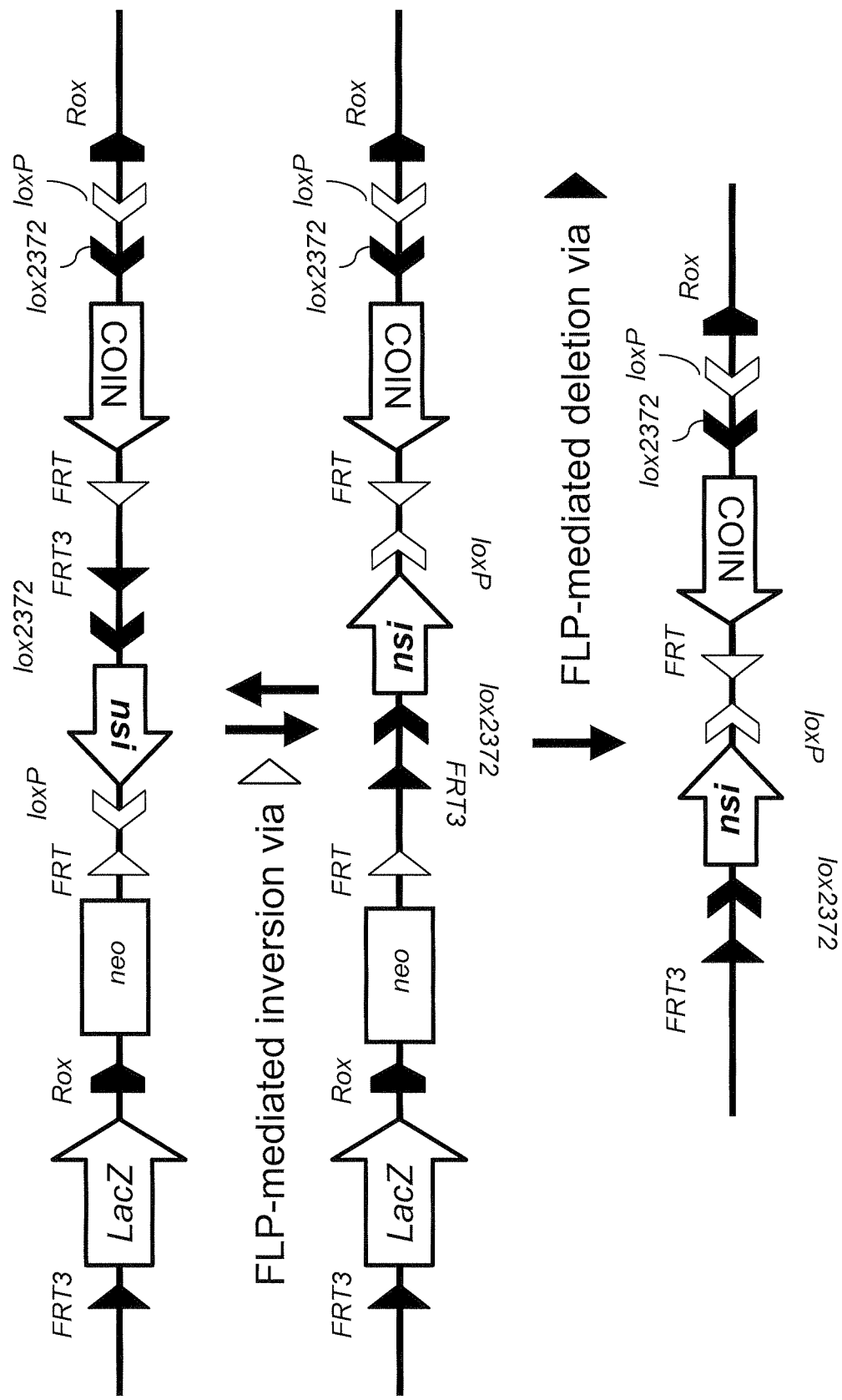
FIG. 6 illustrates an embodiment of an MFA that generates a conditional null allele that contains/incorporates a COIN from an MFA using a single recombinase (here, a Flp recombinase first acting on FRT sites of the allele embodiment). For simplicity, the splice acceptor and splice region preceding the LacZ sequence, and the polyA signal following the LacZ sequence, are not shown.

Although current knockout-first approaches lack a mechanism for reporting nullness upon conversion of a conditional allele to null, the MFA approach provides an option for a reporting element (e.g., a COIN, see FIG. 5 and FIG. 6, at bottom; detectable by genotyping and/or by visualization or other qualitative or quantitative determination, optionally at the cell level) that, upon action of a second recombinase inverts or inverts and excises a nucleotide sequence of interest (e.g., an exon and surrounding sequence, NSI in FIG. 5 and FIG. 6) and places the reporting element in sense orientation, effectively reporting the inversion and/or excision of the NSI. In this embodiment, a null allele following a single targeting step is converted, by a first recombinase to a restored allele (in this embodiment, NSI of FIG. 5 and FIG. 6 is an exon and surrounding sequence or gene or part thereof replaced by the targeting vector), and by a second recombinase to a null allele that reports its presence by placement of the COIN in sense orientation.

Thus the MFA approach provides an option for assessing a phenotypic effect of a knockout (following the targeting step), then exposing to a first recombinase to re-establish the knocked out exon or gene or region thereof, assessing the phenotypic effect of the reestablishment—i.e., conversion back to wild type (a step equivalent to a complementation assay but devoid of the requirement of generating a new transgenic mouse line, a requirement which has traditionally accompanied complementation analysis), then optionally exposing to the second recombinase to reestablish the knockout and assessing the phenotypic effect of reestablishing the null allele. Thus, the MFA allele combines a true knockout-first approach with the versatility of additional (conditional) elements, and the ability to conduct a true complementation-type analysis in a genetically modified animal in a protocol that comprises a single targeting step.

In one MFA application, a method is provided for a complementation assay, comprising targeting an endogenous allele of a cell with an MFA in accordance with the invention, then in a post-targeting step, generating a conditional-null allele from the MFA (by exposure to a first recombinase), wherein the nucleotide sequence of interest in the MFA comprises an exon or an exon plus surrounding sequence, or another region of interest (associated with, e.g., a phenotype) in the sense orientation, and assessing a phenotypic effect of the conditional-null allele (which should be wild type). In a further embodiment, the MFA is further exposed to a second recombinase that reestablishes nullness, and optionally a phenotypic effect is again measured. In a specific embodiment, the second recombinase also places a conditional reporter (e.g., a COIN) in the sense orientation, wherein the conditional reporter reports conversion of the conditional-null allele to a null allele or, as the case may be, reports the reestablishment of nullness.

In one embodiment, the NSI comprises an exon and neighboring intronic sequence, or an exon-intron region of a target gene. In another embodiment, the NSI comprises a region encoding an ncRNA, microRNA, microRNA cluster, or other small ncRNA(s).

MFAs are alleles that can be placed randomly or targeted at a locus of choice in a genome. The MFA is engineered to produce null, conditional, or combination conditional/null alleles by a judicious placement of the sequences among an array of pairs of cognate site-specific recombinase recognition sites. Resulting alleles produced by the placement of constructs in a genome are manipulable by selected recombinases, which can be introduced to the construct in the genome transiently or through breeding of an animal comprising the construct in its genome with an animal comprising a gene for a selected recombinase (e.g., a Cre-, Flp-, or PhiC31 \int-expressing strain).

In various embodiments, methods and compositions are provided for generating a true knockout-first allele where nullness does not depend upon carrying out a second step such as, e.g., removing a "critical exon," or "critical region," by the action of a recombinase. Accordingly, embodiments are provided for generating in a single targeting step an allele that is multifunctional, in that it is a true knockout-first allele with a reporter, achieved in a single targeting recombination step.

The methods and compositions for generating knockout alleles by the MFA approach are not limited by a requirement to generate a frameshift via deletion of inversion of a critical exon to generate a null allele, as required by some types of knockout alleles (e.g., KO-first or some embodiments of FIEx). Instead, the MFA method relies on its ability to remove the NSI from the transcriptional unit of the target gene at the time of targeting, while simultaneously replacing the expression of the NSI with that of an actuating sequence. The actuating sequence can comprise a GT-like element (e.g., a reporter such as SA-lacZ-polyA), a cDNA, an exon or exons, regulatory elements (e.g., enhancers, insulators, operators). Since the actuating sequence is experimenter-defined, alleles other than null can equally well be rendered. For example, the actuating sequence may encode for a dominant-negative or a constitutively active or an activated form of a gene.

In various embodiments the MFA comprises a nucleotide sequence of interest and a COIN that are each in antisense orientation in the resulting allele, and further comprising an actuating sequence and/or a DSC both in sense orientation in the allele (or in sense and antisense orientations, or each independently in sense or antisense orientation), whereupon following exposure to a first recombinase the actuating sequence and/or DSC are deleted, the nucleotide sequence of interest is inverted to a sense orientation, and the COIN is maintained in the antisense orientation. The allele further comprises recombination sites positioned so as to allow for subsequent simultaneous inversion by a second recombinase of the nucleotide sequence of interest and the COIN, such that upon action of the second recombinase the nucleotide sequence of interest is placed in antisense orientation and the COIN is placed in sense orientation. In a further embodiment, the nucleotide of interest is deleted upon treatment with the second recombinase, leaving the COIN in sense orientation. In a specific embodiment, the COIN is a reporter or a DSC. In another specific embodiment the nucleotide of interest is an exon or region of interest of a gene of one specie (e.g., mouse, rat, non-human primate, or human exon) and the COIN is an exon of a gene of another specie (e.g., a mouse, rat, non-human primate, or human exon).

The MFA approach also allows for a gene trap approach. In this embodiment of the MFA approach, an MFA is inserted at a transcriptionally active locus. This may be achieved by random recombination, or by "targeted trapping" (see, e.g., U.S. Pat. No. 7,473,557, hereby incorporated by reference). An actuating sequence preceded by a splice acceptor and splice region and followed by a polyA signal affords a knockout or "knockdown" of any existing transcribed genomic sequence. Inclusion of a promoterless DSC, i.e. one whose expression is dependent on insertion within the sense strand of a transcriptionally active locus, assures positive selection of cells containing the MFA. Inclusion of a nucleotide sequence of interest (NSI) in antisense orientation, along with a COIN in antisense orientation, in conjunction with a recommended arrangement of site-specific recombinase recognition sites, affords the ability to conditionally express the NSI (from the promoter of the trapped locus), upon exposure to a first recombinase. Then, upon exposure to a second recombinase, the expression of the NSI can be turned off and simultaneously replaced by that of the COIN. The promoterless DSC will ensure that any cell selected will have the ability to express the promoterless NSI and the promoterless COIN, and that expression will be in accordance with the endogenous pattern of expression from the transcriptionally active locus.

Certain advantageous approaches using MFAs are conveniently described in connection with particular embodiments (i.e., with reference to alleles comprising specific named recombinase sites and nucleotide sequences as shown in the figures) for convenience and not by way of limitation, i.e., suitable recombinases and recombinase recognition sites, actuating sequences, reporters, DSCs, and nucleotide sequences of interest can be routinely chosen based upon the disclosure herein. The "nucleotide sequence of interest" or "NSI" can be any nucleotide sequence of interest, e.g., an exon, an exon plus flanking sequence(s), two or more exons, a fragment of a coding sequence, an entire coding sequence, a regulatory element or sequence, an non-protein coding sequence, an intron, or any combinations thereof, etc. COINs can comprise cDNAs as well as non-protein coding sequences and may incorporate elements such as polyadenylation signals and sites, microRNAs or other non-protein coding RNAs, IRESs, codon-skipping peptides, and any combination thereof. Certain COINs and some systems for using them can be found, e.g., in U.S. Pat. No. 7,205,148.

Methods and compositions for making and using MFAs in any cell, including non-human animal cells, and in non-human animals, are provided. The methods and compositions can be employed using homologous recombination (or random integration) to place useful alleles at any selected site (or random site) in the genome of a cell. The methods and compositions can be used in pluripotent, induced pluripotent, and totipotent cells. Suitable cells for use with the methods and compositions include ES cells, e.g., mouse or rat ES cells. In various embodiments, true KO-first alleles are provided that afford an option for a conditional functionality with an embedded reporter function.

Figure 2:
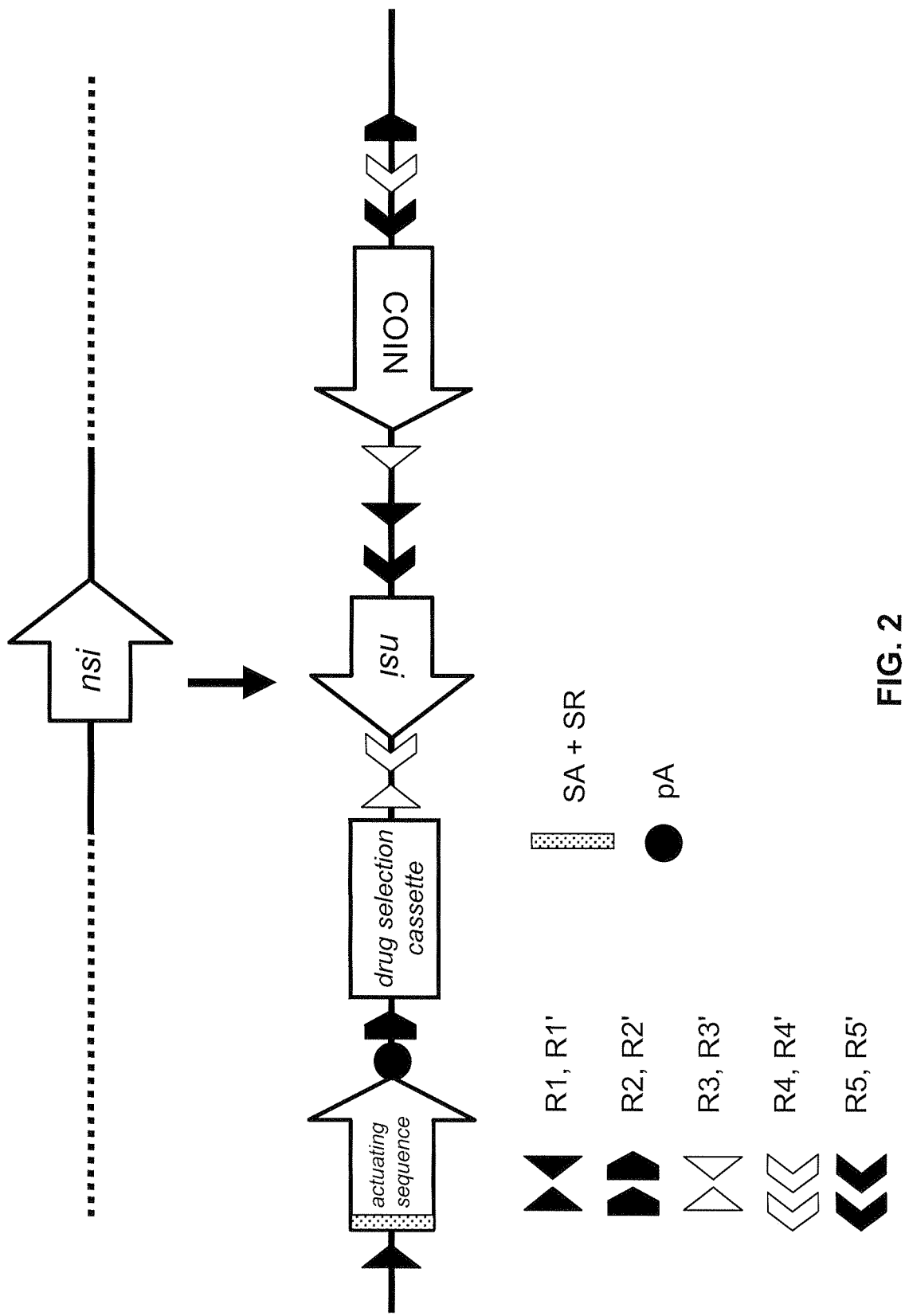
FIG. 2 illustrates an embodiment of a Multifunctional Allele (MFA) allele, shown for a nucleotide sequence of interest (NSI), employing a splice acceptor with splice region and an actuating sequence followed by a polyadenylation (pA) signal, a drug selection cassette (DSC; in a suitable orientation of choice), a COIN, and five pairs of recombinase recognition sites. R1/R1', R2/R2', R3/R3', R4/R4', and R5/R5' represent cognate pairs of recombinase recognition sites.

An example of how an arrangement of elements and recombinase recognition sites can be designed to create a construct that will ablate the function of the target gene (i.e., create a null allele), or alter the function of the target gene (e.g. turning it into a dominant-negative, constitutively active, or hypomorphic allele), while at the same time embed all the downstream elements that will allow (a) the generation of a conditional allele, and (b) it reversion to a null with a reporter, is illustrated in FIG. 2.

FIG. 2 shows an embodiment of an MFA that can be placed into a genome (e.g., using homology arms to the left and right of the MFA shown). Post-targeting, the resulting allele can be converted to a conditional allele, which is accomplished by deleting a first selected sequence and inverting a second selected sequence. The deletion and inversion can be achieved by the same recombinase or a different recombinase. For example, two pairs of incompatible Flp recognition sites can be used—one to direct deletion and the other to direct inversion. One example of two such Flp sites are FRT sites and FRT3 sites. In another example, two pairs of incompatible Cre sites can be used, e.g., loxP and lox2372—one to direct deletion and the other to direct inversion. Further, two different recombinases can be used (e.g., a pair of loxP sites with Cre and a pair of FRT sites with Flp). Any suitable sites can be chosen for this embodiment, so long as the sites can direct deletion and inversion of recombinase site pairs of the MFA shown in FIG. 2 (specific embodiments of which are shown in FIG. 5 and FIG. 6).

Although the construct design of FIG. 2 can be used with any sequences of interest (i.e., NSI is any sequence of interest), the construct design can be particularly useful to replace an exon of interest with a modified exon.

In one embodiment, NSI is a naturally occurring exon (or exons), and the COIN is a modified exon (e.g., an exon comprising a mutation). The MFA is placed into a genome of, e.g., a mouse ES cell by, e.g., homologous recombination (using appropriate mouse homology arms), and the ES cell is employed to make a genetically modified mouse that comprises the construct in the mouse germline. In one embodiment, change of state from the naturally occurring exon to the modified exon is achieved by the action of a recombinase on the MFA.

In one embodiment, the construct is placed in a genome of, e.g., a mouse, and the mouse either further comprises a recombinase (e.g., Cre) whose activity can be regulated. A recombinase can be regulated by, e.g., employing a fusion protein placing the recombinase under control of an effector or metabolite (e.g., CreER$^{T2}$, whose activity is positively controlled by tamoxifen), placing the recombinase under control of a tissue-specific promoter, or placing the recombinase under control of a promoter (or other regulatory element) that is active at a particular developmental stage (e.g., a Nanog promoter), or an inducible promoter (e.g., one whose activity is controlled by doxycycline and TetR or TetR variants), or combinations of these technologies.

The MFA embodiment shown in FIG. 2 bears elements comprising a sequence encoding an actuating sequence, a DSC, a nucleotide sequence of interest (NSI), and a COIN, wherein the elements are arranged among an array of recombinase recognition sites that are selected so as to provide a desired functionality to the MFA.

The top of FIG. 2 illustrates a nucleotide sequence of interest (NSI) in a genome of choice (e.g., an NSI in a mouse genome). An MFA as shown is introduced into the genome by, e.g., homologous recombination to replace the NSI. The NSI is replaced with the MFA shown, where the NSI of the MFA is inverted as shown and thus no longer incorporated into the transcript of the target gene. The presence of the MFA can be conveniently confirmed if the actuating sequence contains a reporter (e.g., a lacZ). A DSC is present as well, to assist in selecting modified cells (e.g., mouse ES cells modified with the MFA).

Figure 3:
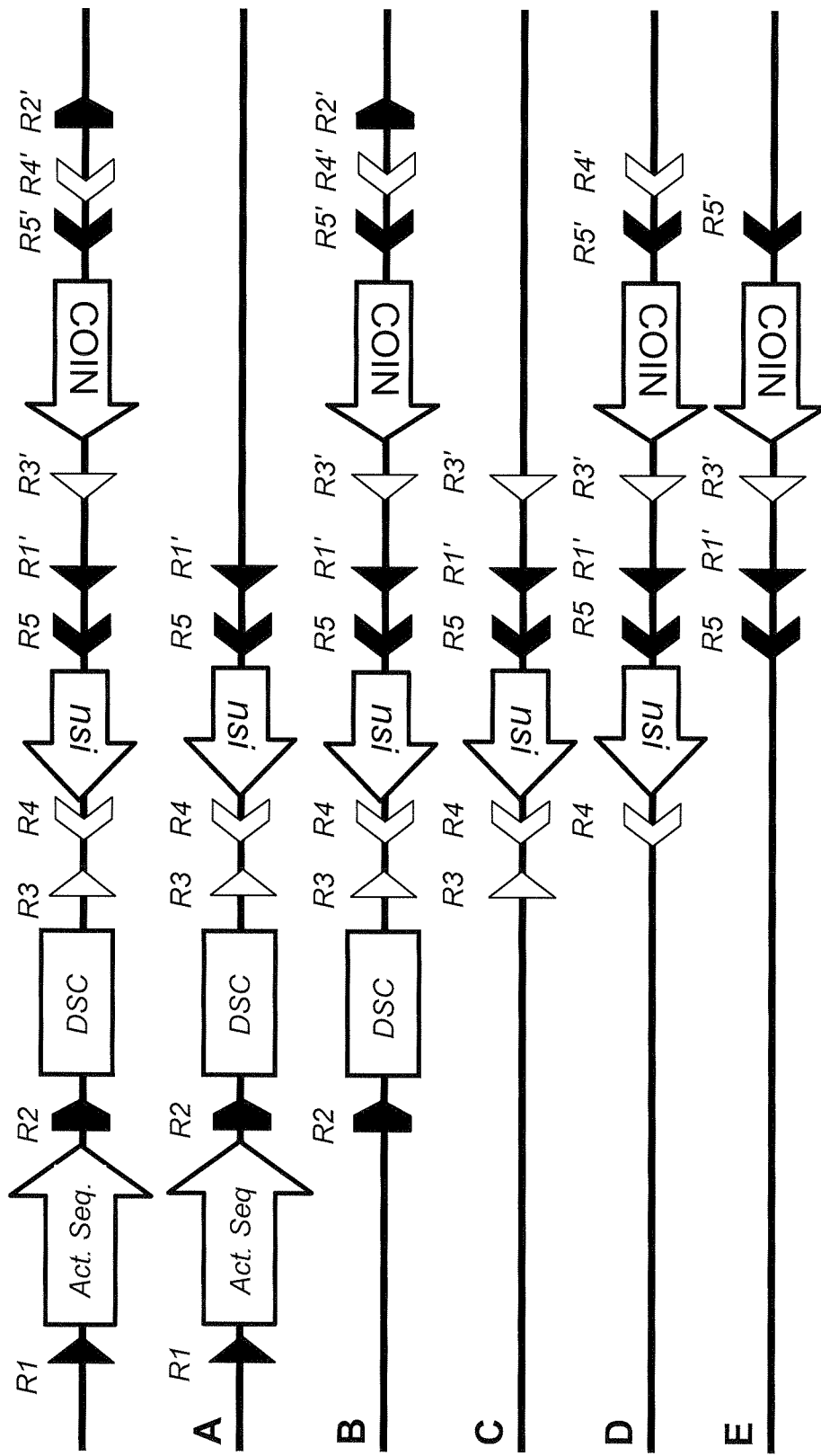
FIG. 3 illustrates a conceptual rendering of recombinable units (defined by R1/R1', R2/R2', R3/R3', R4/R4', and R5/R5') of an embodiment of an MFA allele that employs an actuating sequence (for simplicity the splice acceptor and splice region preceding the sequence, and polyA signal following the sequence are not shown), a DSC (in a suitable orientation of choice), an NSI, and a COIN.

The MFA embodiment of FIG. 2 comprises five distinct units of sequence, defined by five sets of recombinase recognition sites. FIG. 3 contains a conceptual rendering of the five distinct units of sequence flanked by compatible recombinase recognition sites.

The first distinct recombinable unit comprises R1/R1' sites (e.g., FRT3 sites) in opposite orientation (i.e., directing an inversion), wherein between the R1/R1' sites the following are arranged: an actuating sequence (a 3' splice region and acceptor 5' with respect to the actuating sequence, and a polyA signal 3' with respect to the actuating sequence, are not shown in FIG. 3 for the sake of simplicity), an R2 site (e.g., a Rox site), a DSC, an R3 site (e.g., a FRT site) in the same orientation as the R1 site, an R4 site (e.g., a loxP site), and a nucleotide sequence of interest (NSI) in antisense orientation with respect to direction of transcription (i.e., encoded by the antisense strand) of the target gene, and an R5 site (e.g., a lox2372 site) in the same orientation as the R4 site. Where an R3' site (in opposite orientation of the R3 site shown in FIG. 3A) is further included downstream of the 3' R1' site, the unit in the presence of a recombinase that recognizes R1/R1' will invert the NSI into a position for transcription and delete the actuating sequence and DSC. In one embodiment, a further sequence includes a COIN placed on the antisense strand and followed by a R4' site (e.g., loxP site) that is in opposite orientation with respect to the R4 site of the unit, such that upon exposure to a recombinase that recognizes R4/R4' (e.g., Cre), the COIN is inverted such that the coding sequence of the COIN is now in position for transcription downstream of the NSI.

The second distinct recombinable unit (FIG. 3B) comprises R2/R2' sites (e.g., Rox sites) in the same orientation (i.e., directing a deletion), comprising the following sequences disposed between the R2/R2' sites: a DSC, a first R3 site (e.g., a first FRT site) in the same orientation as the R1 site of the first distinct recombinable unit, a first R4 site (e.g., a first loxP site), an NSI in inverted (i.e., antisense) orientation with respect to the target gene, a first R5 site (e.g., a first lox2372 site) in the same orientation with respect to the R4 site, an R1' site (e.g., a second FRT3 site) and an R3' site (e.g., a second FRT site) both in opposite orientation as the R3 site, a COIN (in antisense orientation with respect to transcription of the target gene), an R5' site (e.g., a second lox2372 site) in the same orientation as the R5 site, and an R4' site (e.g., a second loxP site) in the same orientation as R4. This second distinct recombinable unit is excisable by a recombinase that recognizes R2/R2'. When included in the MFA, this unit can be excised to leave behind an actuating sequence (e.g., in some embodiments a reporter, e.g., a sequence encoding lacZ), flanked by an R1 and an R2 or R2' site.

The third distinct recombinable unit (FIG. 3C) comprises R3/R3' sites (e.g., FRT sites) in opposite orientation (i.e., directing an inversion), comprising the following sequences disposed between the R3/R3' sites: an R4 site (e.g., a loxP site), a NSI in inverted (i.e., antisense) orientation with respect to transcription of the target gene, an R5 site (e.g., lox2372 site) in the same orientation as the R4 site of the unit (i.e., of FIG. 3C), and an R1' site (e.g., a FRT site) in the opposite orientation as the R3 site. This unit can be inverted by the action of a recombinase that recognizes R3/R3' (e.g., a Flp recombinase where R3/R3' sites are FRT sites), resulting in placement of the NSI in proper orientation for transcription and translation.

The fourth distinct recombinable unit (FIG. 3D) comprises R4/R4' sites (e.g., two loxP sites) in the same orientation (i.e., directing a deletion), comprising the following sequences disposed between the R4/R4' sites: an NSI in inverted (i.e., antisense) orientation, an R5 site (e.g., a first lox2372 site) and an R1' site (e.g., a FRT3 site) and an R3' site (e.g., a FRT site) each in the same orientation with respect to the R4 site, a COIN (in antisense orientation), and an R5' site (e.g., a second lox2372 site) in the same orientation as the R5 site. In the presence of a recombinase that recognizes R4/R4' (e.g., Cre if R4/R4' are loxP sites, e.g.), this unit is excisable. If placed within the MFA and exposed to the R4/R4' recombinase (in the absence of exposure to a recombinase that recognizes R1/R1', R3/R3'), this unit will be deleted and leave behind the actuating sequence (e.g., in some embodiments a reporter, e.g., a sequence encoding lacZ) and the DSC. Thus, this unit allows for an embodiment in which the MFA, when replacing a sequence in a genome (e.g., replacing an exon), can act in the presence of a recombinase that recognizes R4/R4' as a null allele comprising an actuating sequence and a DSC. The DSC of the MFA can be removed, if desired, upon the action of a recombinase that recognizes R2/R2' (e.g., a Dre recombinase where R2/R2' are Rox sites) because the DSC would be flanked upstream and downstream with R2/R2' sites in the same orientation.

The fifth distinct recombinable unit (FIG. 3E) comprises R5/R5' sites (e.g., two lox2372 sites) in the same orientation (i.e., directing a deletion) as well as in the same orientation of the R4/R4' sites of the fourth distinct recombinable unit, comprising the following sequences disposed between the R5 and R5' sites: an R1' site (e.g., a FRT3 site) and an R3' site (e.g., a FRT site) in the same orientation with respect to each other but in opposite orientation to the R1 site of the first distinct recombinable unit, and a COIN (in antisense orientation) with respect to transcription of the target gene.

As those of skill in the art would recognize, the overlapping recombinable units are so described to convey the structure of the MFA, rather than to limit the possible recombinable elements in the MFA. For example, those skilled in the art will recognize that each recombinable unit comprises site-specific recombination sites within the recombinable unit, and that action of a recombinase on sites (across recombinable units) achieves desired and described manipulations of the MFA that achieve intended functions of the MFA. For example, with reference to FIG. 3, the action of a recombinase that recognizes R1/R1' and R3/R3' functions to manipulate portions of all five recombinable units as they are conceptually displayed in FIG. 3.

Figure 4:
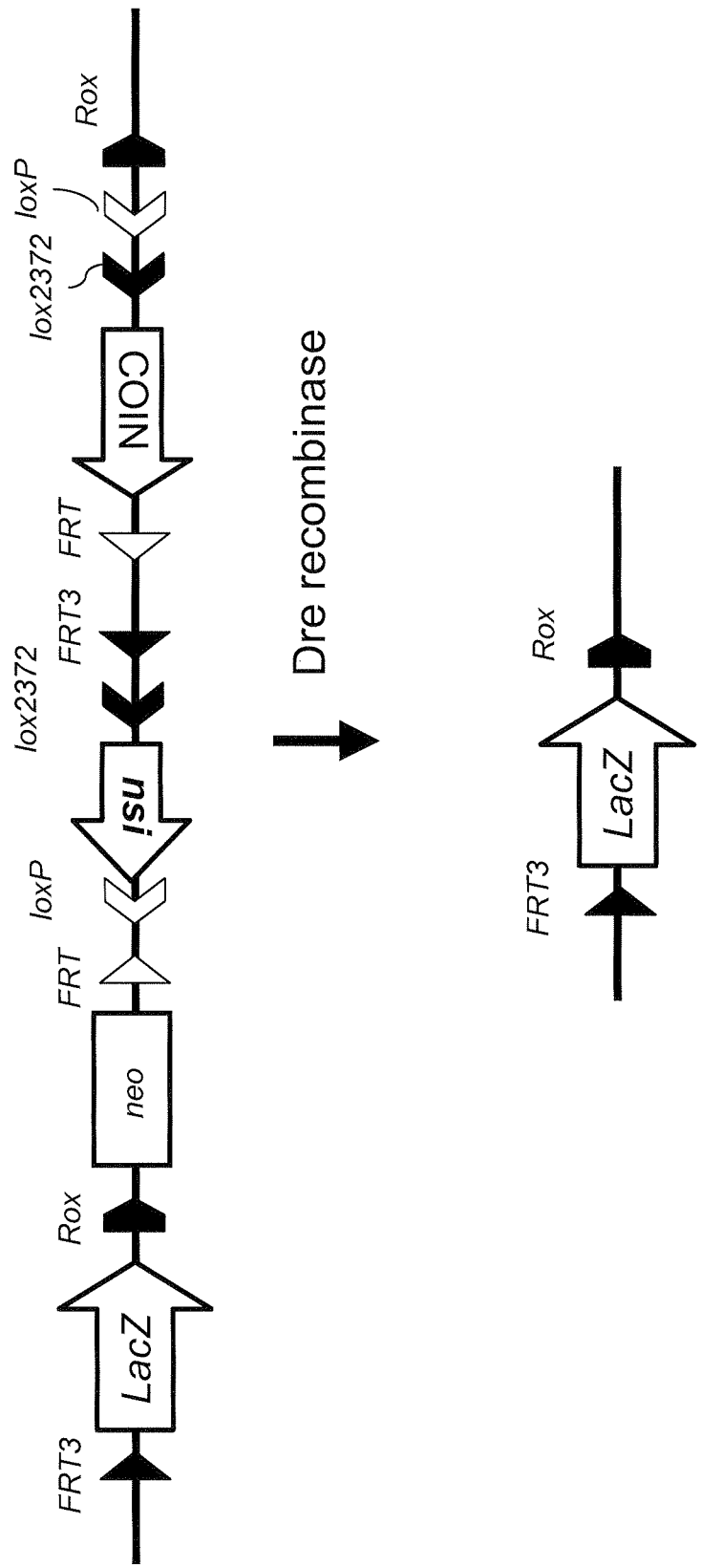
FIG. 4 illustrates a particular embodiment of an MFA with specific recombinase recognition sites for purposes of illustration (top), and generating a "cleaned-up" null allele comprising an actuating sequence that comprises a LacZ sequence, and removing the DSC as well as a the NSI and the COIN element from the initial MFA embodiment using a single recombinase step. For simplicity, the splice acceptor and splice region preceding the LacZ sequence, and the polyA signal following the LacZ sequence, are not shown.

Once an MFA is placed at a desired location in a genome it can be engineered such that it provides a null allele with a reporting function, wherein the null allele can be remodified (in post-targeting, recombinase-mediated step) such that it lacks all sequences flanked with recombinase recognition sites oriented in the same direction. An example of this embodiment is shown in FIG. 4 showing examples of suitable recombinase recognition sites, where all elements other than the actuating sequence (here, encoding lacZ) are flanked upstream and downstream by Rox sites. Upon exposure to Dre recombinase, only the actuating sequence is present. Excision of the Roxed sequences can be confirmed by loss of the DSC (here, containing neo$^r$), and/or loss of the COIN, and/or loss of the NSI. The result is a true null allele that lacks the DSC, NSI, and COIN.

An MFA as illustrated in FIG. 2 and as exemplified at the top of FIG. 3 can be used to create a conditional allele. A conditional allele can be generated by selecting the appropriate recombinase with which to expose the allele in the first instance. The appropriate recombinase in this embodiment is a recombinase that inverts the NSI back to the sense strand and leaves the COIN in the antisense orientation. This can be achieved, e.g., by exposing the MFA to a recombinase that recognizes R1/R1' and also R3/R3' (e.g., a Flp recombinase where R1/R1' and R3/R3' are selected from FRT and FRT3 sites; see FIG. 5 for a particular embodiment). Briefly, once an MFA is placed at a desired location in a genome, it can be used to generate a conditional allele, wherein the inverted NSI of FIG. 2 and the top of FIG. 3 is disposed in an orientation for transcription of the target gene, while leaving the COIN in antisense orientation and deleting the actuating sequence and DSC. An example of this embodiment is shown in FIG. 5, where an actuating sequence that contains a lacZ and a DSC containing neo$^r$ are removed by first exposing the allele to Flp recombinase, causing an inversion of elements directed by FRT3 sites, followed by Flp-mediated deletion directed by FRT sites. The resulting allele presents the NSI in an orientation for transcription, but leaves the COIN in the antisense orientation.

As shown in FIG. 6, the same conditional allele can be achieved whether Flp-mediated inversion occurs first via FRT sites (as in FIG. 5) or FRT3 sites (as in FIG. 6).

In the embodiment that generates a conditional allele, recombinase sites remaining in the allele are selected such that treatment with one or more suitable recombinases results in subsequent deletion of the NSI (or re-inversion of the NSI) and inversion of the COIN, such that the allele results in a null allele with respect to the NSI but also places the COIN in orientation for transcription. An example of this is shown using loxP and lox2372 sites, which each independently direct Cre-mediated recombination. Although Cre-reactive sites are used, any suitable sites can be used instead of Cre sites.

Figure 7:
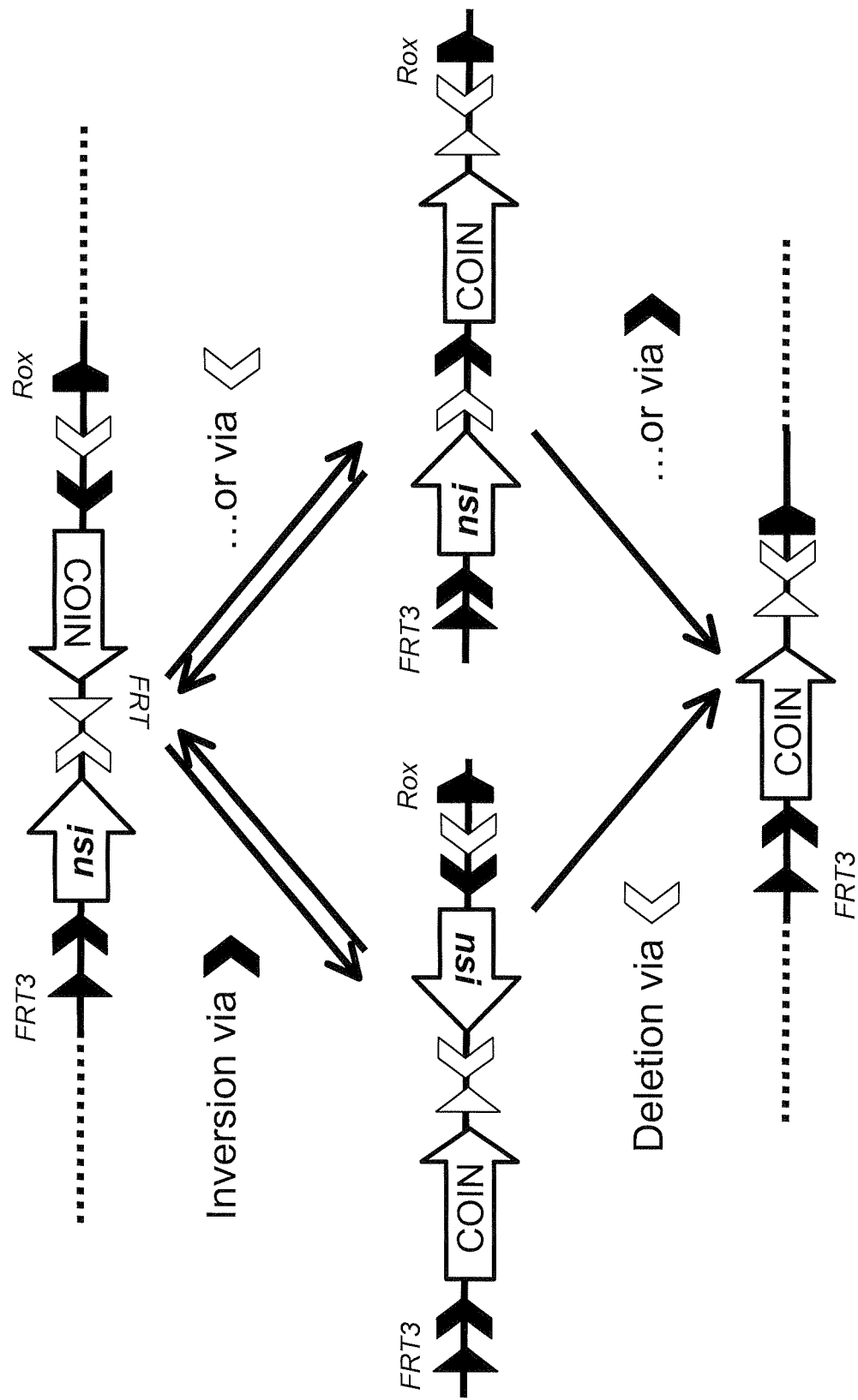
FIG. 7 illustrates an embodiment wherein, following recombinase treatment (Flp exposure as shown in FIG. 5 or FIG. 6), the allele is exposed to a second recombinase (Cre), resulting in deletion of the NSI and placement of the COIN in sense orientation for transcription.

As shown in FIG. 7, the NSI in sense orientation (i.e., in position for transcription and translation) is disposed 3' with respect to a first lox2372 site. Following the NSI is a first loxP site in the same orientation as the first lox2372 site, and an inverted (i.e., antisense) COIN is placed downstream of the first loxP site, and the inverted COIN disposed upstream of a second lox2372 site in opposite orientation with respect to the first lox2372 site. Disposed downstream of the second lox2372 site is a second loxP site disposed in an opposite orientation with respect to the first loxP site. This arrangement allows, upon treatment with Cre, inversion via either lox site followed by deletion via either lox site (see FIG. 7). The resulting allele contains a COIN in sense orientation, i.e., in position for transcription and translation.

Figure 8:
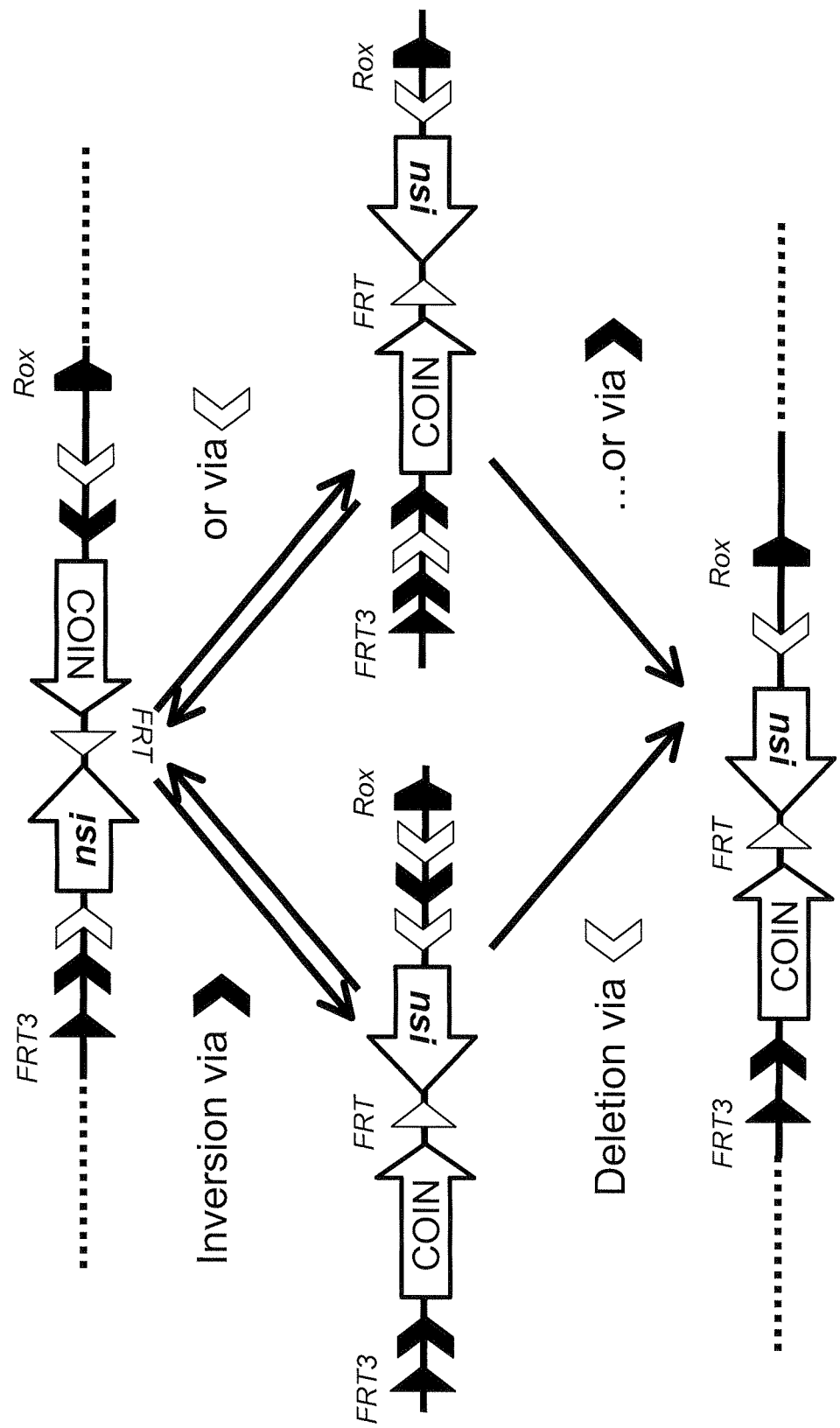
FIG. 8 illustrates an embodiment wherein, following recombinase treatment (Flp exposure), the allele is exposed to a second recombinase, resulting in inversion of the COIN and the NSI due to (an alternative) placement of a recombinase recognition site for the second recombinase at a position 5' of the NSI.

In an alternative arrangement (see FIG. 8), a loxP site is placed 5' with respect to the NSI (instead of disposed between the NSI and the COIN), such that exposure to Cre results in inversion of the NSI to antisense orientation and the COIN to sense orientation.

The MFA approach provides options for many embodiments. In a specific embodiment, upon exposure to the first recombinase, the arrangement of elements and recombinase sites are as shown in the bottom construct of FIG. 5 or FIG. 6, wherein the FRT3 site as shown is site R1 that has no cognate site in the resulting allele, the FRT site as shown is a recombinase site R3 that has no cognate site in the resulting allele, the left-most lox2372 site is site R5 that is paired with a cognate recombinase site R5' occupying the right-most lox2372 site as shown, the left-most loxP site as shown is site R4 that is paired with a cognate recombinase site R4' provided by the right-most loxP site as shown, and the Rox site as shown is site R2 that has no cognate recombinase site in the resulting allele.

In a specific embodiment, upon exposure to the second recombinase, the arrangement of elements and recombinase sites of the resulting allele are as shown in the bottom construct of FIG. 7, wherein the FRT3 site shown is site R1 that has no cognate site in the resulting allele, the lox2372 site is site R5 that is not paired with a cognate recombinase site in the resulting allele, the FRT site shown is site R3 that is not paired with a cognate recombinase site in the resulting allele, the loxP site as shown is site R4 that is not paired with a cognate recombinase site in the resulting allele, and the Rox site as shown is site R2' that is not paired with a cognate recombinase site in the resulting allele.

In a specific embodiment, the resulting allele allows expression of the COIN following exposure to the second recombinase. In a specific embodiment, the COIN is a reporter or a DSC.

In one aspect, an MFA is provided that comprises a COIN, an NSI, a DSC, a reporter, and recombinase sites that are arranged such that action by one recombinase will excise the COIN, the NSI, and the DSC but not the reporter (FIG. 11B), whereas action with a different recombinase will generate an allele that lacks the DSC but that places the NSI in sense orientation while maintaining the COIN in antisense orientation (FIG. 11C). This resulting allele has recombinase sites arranged such that action by a further recombinase will excise the NSI and place the COIN in sense orientation (FIG. 11D). Thus, in the embodiments discussed, this MFA will allow selection of a true knockout with a reporter function and removal of the DSC, or placement of an NSI, wherein subsequent removal of the NSI is confirmed by concomitant placement of a COIN in sense orientation. A schematic of some overlapping recombinase units are shown in FIG. 11A for such an allele, with like recombinase units represented by like dashed shapes.

In one aspect, an MFA is provided that comprises a COIN, an NSI, a DSC, a reporter, and recombinase sites that are arranged such that action by one recombinase will excise the NSI and DSC but maintain the orientation of the reporter and COIN (FIG. 12B), whereas action with a different recombinase will generate an allele that lacks the DSC and reporter but that places the NSI in sense orientation while maintaining the COIN in antisense orientation (FIG. 12C). This resulting allele has recombinase sites arranged such that action by a further recombinase will excise the NSI and place the COIN in sense orientation (FIG. 12D). Thus, in the embodiments discussed, this MFA will allow selection of a true knockout with a reporter function and removal of the DSC; or placement of an NSI, wherein subsequent removal of the NSI is confirmed by concomitant placement of a COIN in sense orientation. A schematic of some overlapping recombinase units are shown in FIG. 12A for such an allele, with like recombinase units represented by like dashed shapes.

In one aspect, an MFA is provided that comprises a COIN, an NSI, a DSC, a reporter, and recombinase sites that are arranged such that action by one recombinase will excise the reporter and DSC and place the NSI in sense orientation (FIG. 13B). This resulting allele has recombinase sites arranged such that action by a further recombinase will place the NSI in antisense orientation while placing the COIN in sense orientation (FIG. 13C). Thus, in the embodiments discussed, this MFA will allow creation of a conditional allele from an MFA.

In one aspect, an MFA is provided that comprises a COIN, and NSI, a DSC, a reporter, and a different array of recombinase sites that are arranged such that action by a selected recombinase will excise the reporter and the DSC and place the NSI in sense orientation (FIG. 14B). This resulting allele has recombinase sites arranged such that action by a further recombinase will place the NSI in antisense orientation while placing the COIN in sense orientation (FIG. 14C). Thus, this MFA will also allow creation of a conditional allele from an MFA.

In one aspect, an MFA is provided that comprises an NSI, a DSC, a reporter, a COIN, and recombinase sites that are arranged such that action by a selected recombinase will excise the reporter and the DSC and place the NSI in sense orientation while maintaining the COIN in antisense orientation (FIG. 15B). This resulting allele has recombinase sites arranged such that action by a further recombinase will place the NSI in antisense orientation while placing the COIN in sense orientation (FIG. 15C). Thus, this MFA will also allow creation of a conditional allele from an MFA.

EXAMPLES

Example 1: Hprt1 MFA

Figure 9:
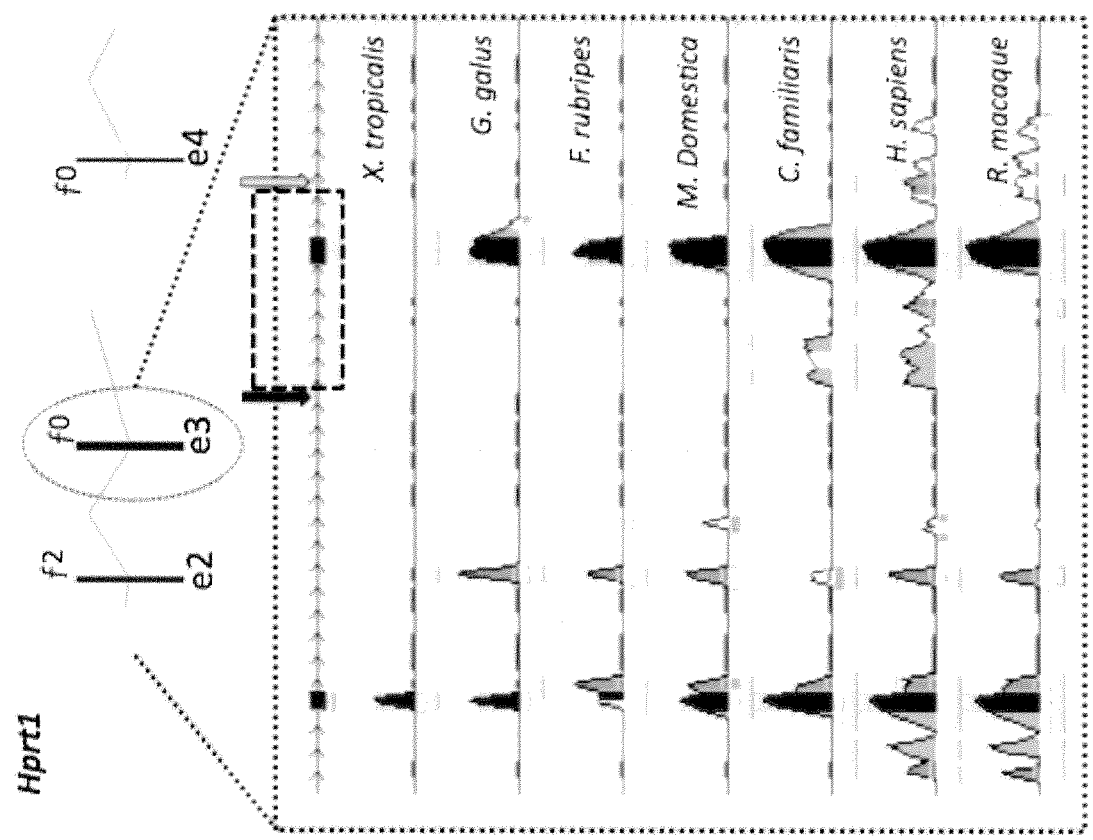
FIG. 9 illustrates the exon-intron structure of the mouse Hprt1 gene in the region of exons 2 to 4, adapted from the Ensembl mouse genome server (top panel—www.ensembl.org), and the region from exon 2 to exon 4 is expanded in the ECR browser (http://ecrbrowser.dcode.org) to highlight regions of conservation. Exon 3 is highlighted by a dotted oval. The black vertical arrow indicates the point of insertion of the actuating sequence and DSC, whereas the gray arrow indicates the point of insertion of the COIN element, all used to engineer the Hprt1$^{MFA}$ allele. Note that none of the evolutionarily conserved intronic sequences flanking exon 3 are disrupted in the resulting allele. The dotted parallelogram denotes the region that will become the NSI in the Hprt1$^{MFA}$ allele.
Figure 10:
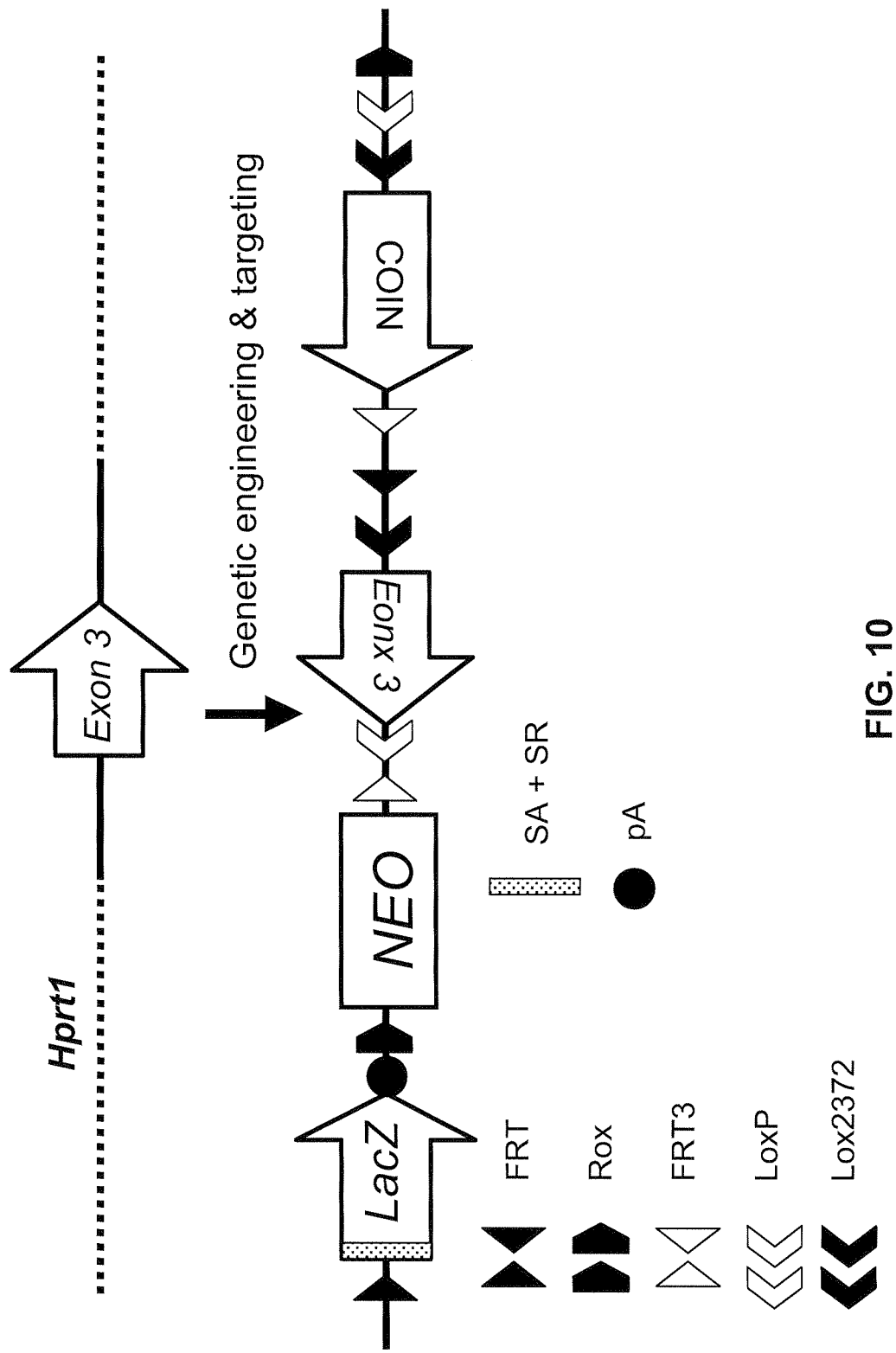
FIG. 10 illustrates an example of an MFA, specifically the MFA for the Hprt1 gene. Exon 3 plus evolutionarily conserved intronic sequences flanking exon 3 (as illustrated in FIG. 9) of Hprt1 become the NSI. Upon targeting, the NSI is placed into the antisense strand with respect to the direction of transcription of the Hprt1 gene. An actuating sequence—SA-lacZ-polyA—and a DSC are placed upstream of the NSI. The actuating sequence is placed in the sense orientation with respect to the direction of transcription of the Hprt1 gene, effectively acting as a gene-trap element, and abrogating transcription downstream of the actuating sequence. A COIN element is placed downstream of the NSI in the antisense orientation with respect to the direction of transcription of the Hprt1 gene. Neither the COIN element nor the NSI can be incorporated into a productive Hprt1 mRNA and therefore the resulting allele, Hprt1$^{MFA}$, is a null allele with a reporter (LacZ). The elements comprising the Hprt1$^{MFA}$ allele are flanked by site-specific recombinase recognition sites arranged as follows: FRT-actuating sequence-Rox-DSC-FRT3-(LoxP)-(NSI)-(Lox2372)-(FR7)-(FRT3)-(COIN)-(Lox2372)-(LoxP)-Rox, where parenthesis denotes placement in the antisense orientation with respect to the direction of transcription of the Hprt1 gene, or in the case of site-specific recombinase sites opposite orientation with respect to mutually recognized pairs.

Hprt1 is a gene that is X-linked in mice, and Hprt1-null ES cells are resistant to the nucleobase analog 6-thioguanine (6-TG). This property provides an easy and robust phenotypic test, as cells that are wild type for Hprt1 die in the presence of 6-TG, whereas cells that are null for Hprt1 survive. Additionally, if one targets ES cells that are derived from male blastocysts (as is typically the case, and is also the case for the majority of ES cell lines currently in use for targeting), then only one round of targeting is needed to generate $Hprt1^{MFA}/Y$ ES cells. In order to generate $Hprt1^{MFA}/Y$ ES cells, an MFA in a targeting vector, according to the allele shown in FIG. 5 (top), is prepared by standard genetic engineering methodology and bacterial homologous recombination according to the VELOCI-GENE® method described in U.S. Pat. No. 6,586,251 and in Valenzuela et al. (2003) High-throughput engineering of the mouse genome coupled with high-resolution expression analysis, Nature Biotech. 21(6):652-659 (the patent and article are hereby incorporated by reference). The $Hprt1^{MFA}$ allele is designed around exon 3, defining exon 3 and the conserved intronic sequence directly 5' and 3' of it as the NSI (FIG. 9). The reason for this choice lies in that exon 3 begins in frame 2 (f2) and ends in frame 0 (f0); by extension, the preceding exon exon 2) ends in frame 2 (f2), and the following exon exon 4) begins in frame 0 (J0). This means that if this NSI is inverted into the antisense orientation, then exon 2 is rendered out of frame with respect to exon 4, because exon 2 ends in f2 and exon 4 starts in f0. In this manner, if in the $Hprt1^{MFA}$ allele there is any transcription past the actuating sequence—SA-lacZ-polyA (FIG. 10)—and there is also splicing that removes the actuating sequence from the final mRNA, that mRNA will not comprise exon 3 and will encode a nonsense sequence, effectively giving rise to an Hprt1-null mRNA and phenotype. Conversely, for the $Hprt1^{COIN-INV}$ allele (generated by treatment of $Hprt1^{MFA}$ with FLP or variants of FLP to first generate the $Hprt1^{COIN}$ allele, then by treatment with Cre to generate $Hprt1^{COIN-INV}$) if there is transcription past the SA-eGFP-polyA of the COIN element (FIG. 10), and there is also splicing that removes the SA-eGFP-polyA sequence from the final mRNA, that mRNA will not comprise exon 3 and therefore will encode a nonsense sequence, effectively giving rise to an Hprt1-null mRNA and phenotype.

The antisense-oriented NSI is exon 3 and surrounding evolutionarily conserved intronic sequence of Hprt1 (FIG. 9), and the antisense-oriented COIN is a SA-eGFP-polyA. The targeting vector has a mouse homology arm upstream of the first FRT3 site and downstream of the second Rox site that direct the targeting into the Hprt1 locus such that it is replaced by its MFA version, whereby (a) a SA-LacZ-polyA element in the sense orientation with respect to the direction of transcription of Hprt1, followed by a DSC in the antisense orientation with respect to the direction of transcription of Hprt1, both preceding exon 3 of Hprt1, (b) exon 3 is placed into the antisense orientation with respect to the direction of transcription of Hprt1, and (c) a COIN element is placed in the antisense orientation with respect to the direction of transcription of Hprt1 downstream of the exon 3, and where these different elements are flanked by site-specific recombinase recognition sites, together arranged in recombinable units as detailed in FIG. 3 and FIG. 10, with SA-LacZ-polyA being the actuating sequence, and exon 3 plus flanking intronic sequences of Hprt1 being the NSI.

The targeting vector is prepared and electroporated into ES cells according to the VELOCIGENE® method described in U.S. Pat. No. 6,586,251 and in Valenzuela et al. (2003) High-throughput engineering of the mouse genome coupled with high-resolution expression analysis, Nature Biotech. 21(6):652-659 (the patent and article are hereby incorporated by reference). The resulting ES cells bear the MFA allele of Hprt1 in place of the wild type version of Hprt1. Prior to any further modification the Hprt1$^{MFA}$/Y ES cells are resistant to treatment with 6-TG (because they are effectively null for Hprt1), demonstrating the usefulness of the MFA method to generate a true knockout-first allele. After treatment with Dre, this property is preserved, while the genotype of the cells is converted to Hprt1$^{SA-LacZ-polyA}$/Y. Although for the Hprt1 locus, this modification may neither alter the expression level of the reporter (LacZ) nor have any phenotypic consequences (alter resistance to 6-TG), this may not be the case for other loci. After treatment with FLP or FLP variants, in a step that is effectively equivalent to a complementation test, the Hprt1$^{MFA}$/Y ES cells are converted to Hprt1$^{COIN}$/Y ES cells which are effectively wild type and hence sensitive to 6-TG. In addition, this operation restores expression of the Hprt1 message back to its wild-type identity. After treatment with Cre, the Hprt1$^{COIN}$/Y ES cells are converted to Hprt1$^{COIN-INV}$/Y ES cells which are effectively null for Hprt1 and hence resistant to 6-TG. In addition, this operation results in abrogation of expression of the wild-type message of Hprt1 message, and its concomitant replacement with a hybrid message composed of the first exon of Hprt1 and eGFP (encoded by the COIN element), thereby generating an allele that expresses eGFP in place of Hprt1. This new property, expression of eGFP, can be optionally used to score for inversion of the COIN element to the sense strand, and has further utility in enabling the isolation of cells where this event has taken place from a cell population where both types of cells (Hprt1$^{COIN}$/Y ES cells, and Hprt1$^{COIN-INV}$/Y ES cells) exist. Therefore, not only is the COIN allele converted into a null, but the event is also marked by a new, easily measurable and useful event.

Example 2: Hprt1 MFA Results

An MFA having a LacZ reporter (SA(adm1)-gtx-LacZ-pA) in sense orientation, a neomycin DSC (Neo), an NSI in antisense orientation that encompasses a critical exon ($e_c$) for Hprt1 (exon 3) and flanking evolutionarily conserved intronic sequences, and a COIN (Gtx-SA-HA-myc3-TM-T2A-GFP-pA) was constructed with an arrangement of recombinase sites as shown in FIG. 16A. The MFA was electroporated into F1H4 ES cells and were selected for resistance to G418. Subsequently, G418-resistant colonies were genotyped to determine targeting. Five targeted clones (Hprt1$^{MFA}$/Y) were obtained from a total of 96 colonies screened. All five of these clones were found to survive and propagate when cultured in standard ES cell media supplemented with 10 μM 6-TG (which is the standard 6-TG survival assay utilized), as would be expected for cells that are Hprt1-null (Doetschman, T. et al. (1987) Targeted correction of mutant HPRT gene in mouse embryonic stem cells, Nature 330:576-578). In contrast, the parental cell line, F1H4, as well as any of the non-targeted clones that were tested, failed to grow in the presence of 6-TG. These results are in agreement with what has been reported previously (Doetschman et al. (1987)).

Upon treatment with recombinase FLPo (Raymond, C. S. and Soriano, P. (2007) High-efficiency FLP and PhiC31 site-specific recombination in mammalian cells, PLoS ONE 2:e162), the Hprt1$^{MFA}$ allele is converted to the Hprt1$^{COIN}$ allele (FIG. 16B), giving rise to Hprt1$^{MFA}$/Y ES cells. This operation results in removal of the LacZ reporter, the DSC, as well as in re-inversion of the NSI into the sense strand. Therefore, the resulting allele (Hprt1$^{COIN}$) is functionally wild type, as the wild type Hprt1 mRNA is encoded and expressed.

On further treatment with recombinase Cre (Sauer, B. and Henderson, N. (1988) Site-specific DNA recombination in mammalian cells by the Cre recombinase of bacteriophage P1, Proc. Natl. Acad. Sci. USA 85:5166-5170), the Hprt1$^{COIN}$ allele is converted to the Hprt1$^{COIN-INV}$ allele (FIG. 16C), giving rise to Hprt1$^{COIN-INV}$/Y ES cells. This allele (Hprt1$^{COIN-INV}$) is functionally null, as the Hprt1 mRNA is replaced by one encoding eGFP (and is also lacking the NSI—i.e., Hprt1's exon 3 and flanking intronic sequences as defined at the design stage).

Figure 16:
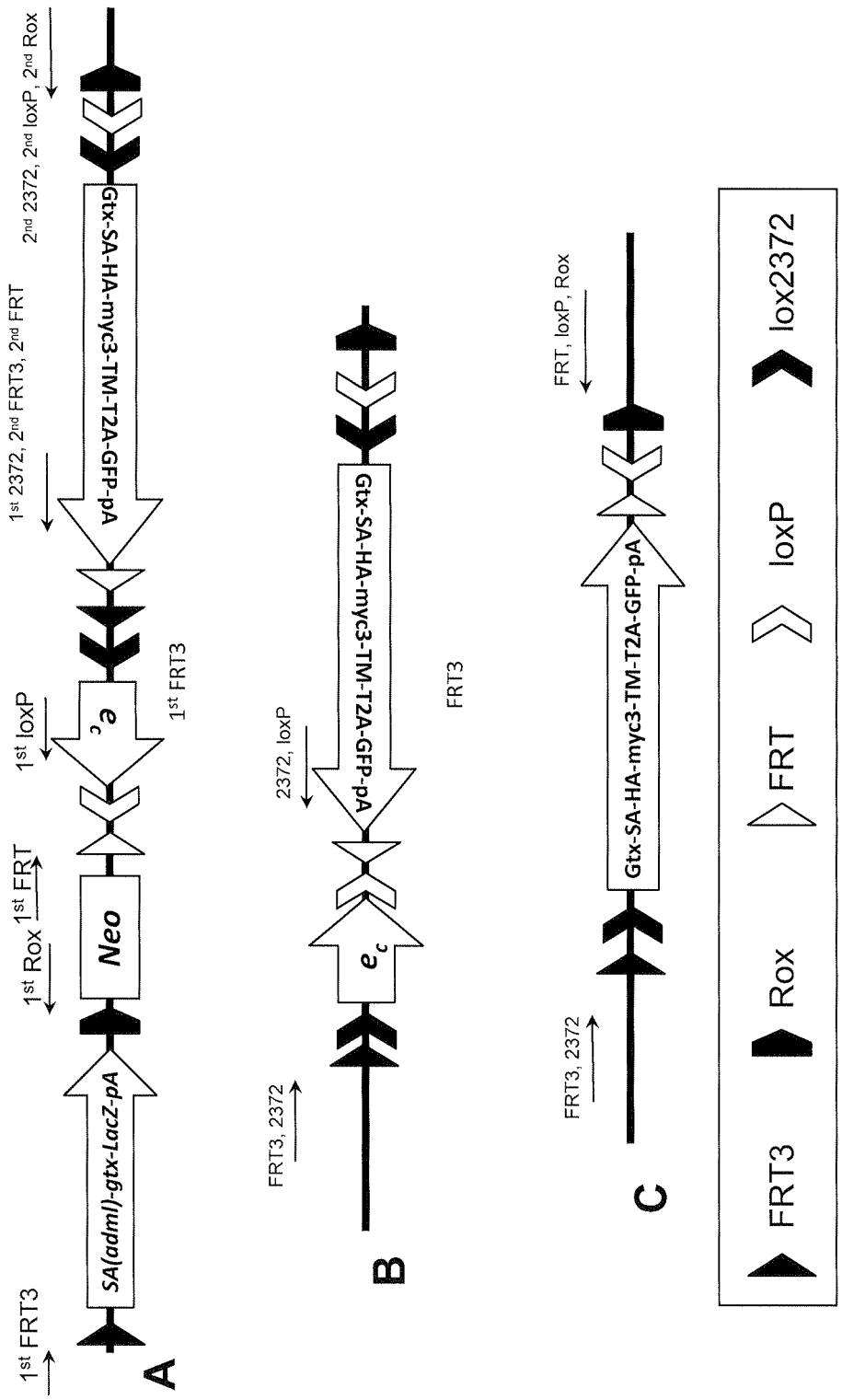
FIG. 16 illustrates an example of an MFA embodiment, wherein the reporter is a SA(adml)-gtx-LacZ-pA, the DSC is Neo, the NSI is a critical exon ($e_c$), and the COIN is Gtx-SA-HA-myc3-TM-T2A-GFP-pA (A), placement of the NSI in sense orientation by action of a recombinase while maintaining the COIN in antisense orientation (B), and further excision of the NSI with concomitant placement of the COIN in sense orientation (C); arrows indicate primers used to confirm identities and orientations of recombinase sites in the MFA (A), and upon recombinase treatment (B and C).
Figure 17:
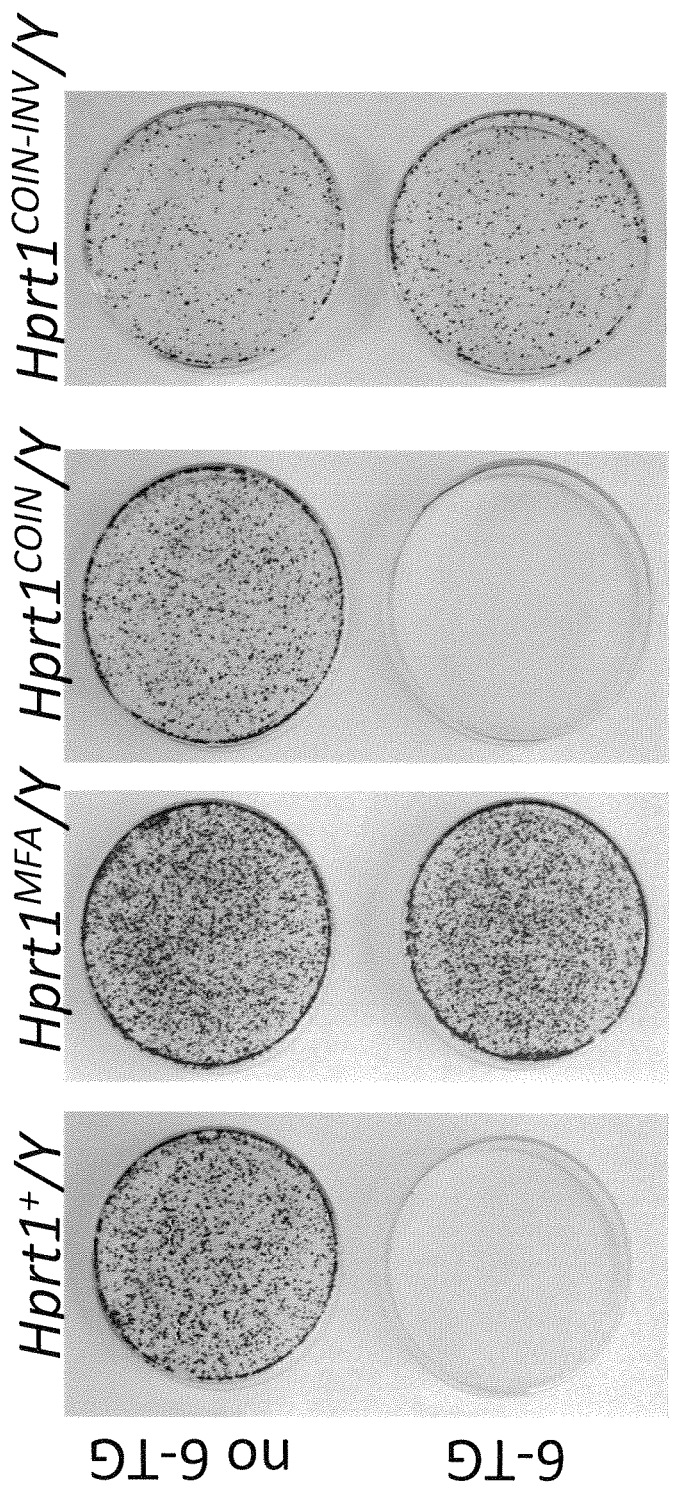
FIG. 17 shows the results of cell viability and proliferation assays for Hpr1$^+$/Y, Hpr1$^{MFA}$/Y, Hpr1$^{COIN}$/Y, and Hprt1$^{COIN-INV}$/Y ES cells respectively, all cultured in standard ES cell culture media either without 6-TG (no 6-TG; upper panels) or supplemented with 10 μM 6-TG (6-TG; lower panels).
Figure 18:
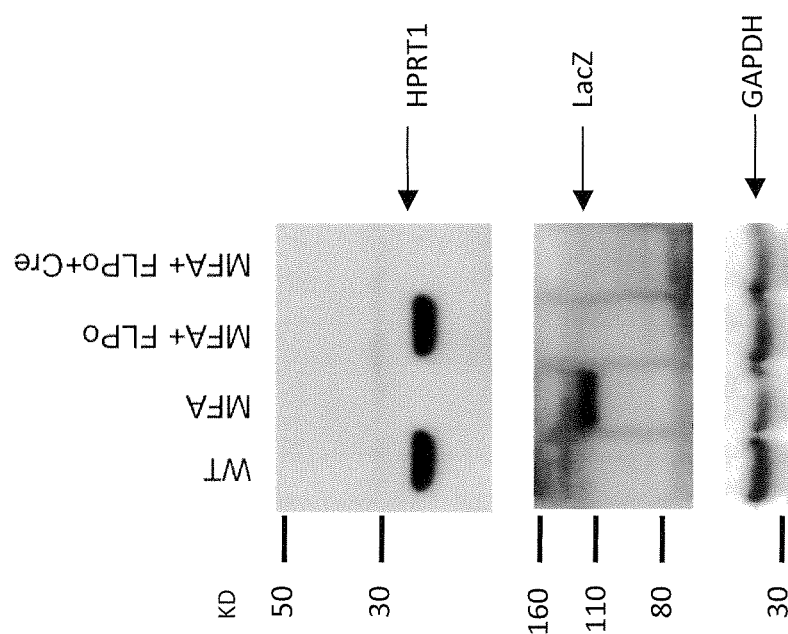
FIG. 18 shows Western blots of total protein preparations derived from Hprt1$^+$/Y cells (WT), Hprt1$^{MFA}$/Y (MFA)—i.e. cells targeted with the MFA of FIG. 16A, Hprt1$^{COIN}$/Y cells (MFA+FLPo)—i.e. cells targeted with the MFA of FIG. 16A and then treated with FLPo, and Hprt1$^{COIN-INV}$/Y cells (MFA+FLPo+Cre)—i.e. Hprt1$^{COIN}$/Y cells treated with Cre; the top panel shows detection of Hprt1 protein, the center panel shows detection of LacZ (reporter) protein, and bottom panel shows detection of GAPDH protein as a loading control.

Cells bearing the MFA (Hprt1$^{MFA}$/Y) were tested for resistance to the nucleotide analog 6-TG, and were compared with wild-type cells (FIG. 17). The Hprt1$^{MFA}$/Y ES cells survived whereas the Hprt1$^{+}$/Y ES cells died, indicating that the Hprt1$^{MFA}$/Y are functionally Hprt1-null. Hprt1$^{MFA}$/Y ES cells were then treated with FLPo, to test if the Hprt1$^{MFA}$ allele would be converted to the Hprt1$^{COIN}$ allele. The resulting Hprt1$^{COIN}$/Y ES cells are expected to be phenotypically wild type, as Hprt1 expression is restored. This was shown to indeed be the case, as Hprt1$^{COIN}$/Y ES cells die when cultured in the presence 6-TG, just like their wild type (Hprt1$^{+}$/Y) counterparts. Finally, the Hprt1$^{COIN}$/Y ES cells were treated with Cre to generate Hprt1$^{COIN-INV}$/Y ES cells, which are predicted to be null for Hprt1 as the COIN module is activated while simultaneously deleting Hprt1's exon 3 (FIG. 16, Panel C). When cultured in the presence of 6-TG, the Hprt1$^{COIN-INV}$/Y ES cells survived and proliferated, confirming that they are functionally null for Hprt1, as intended by the MFA design and application.

The phenotypic results obtained above where further confirmed at the protein level, by performing Western blots on protein preparations of ES cells belonging to each genotypic class: wild-type (Hprt1$^{+}$/Y), Hprt1$^{MFA}$/Y (MFA), Hprt1$^{COIN}$/Y (MFA+FLPo), and Hprt1$^{COIN-INV}$/Y (MFA+FLPo+Cre). These protein preparations were examined for reporter and NSI (i.e., Hprt1) expression. Hprt1$^{MFA}$/Y ES cells lack Hprt1 protein, but express the reporter (LacZ). In Hprt1$^{COIN}$/Y ES, expression of Hprt1 is restored to wild type levels, reflecting the placement of the NSI (exon 3 of Hprt1) back into the sense orientation, and did not show reporter (LacZ) protein, confirming reporter excision by FLPo. This established that the Hprt1$^{MFA}$ allele is indeed null, and can be converted to a functional wild type allele after removal of the reporter and DSC, and concomitant re-inversion of the NSI into the sense strand (an operation experimentally accomplished by FLPo). The fact that at the level of Hprt1 protein expression the Hprt1$^{COIN}$ allele is identical to wild type (Hprt1$^{+}$), further demonstrates the robustness of this method to generate a true conditional-null and perform the equivalent of a complementation assay in one, recombinase-mediated, post-targeting step. Finally, the Hprt1$^{COIN-INV}$/Y ES cells lack Hprt1 protein, effectively confirming the phenotypic observations made using the 6-TG resistance assay. This further confirms that the COIN-based conditional-null allele (Hprt1$^{COIN}$) functions as intended.

We claim:

1. A nucleic acid construct, comprising:
    (a) targeting arms for directing the nucleic acid construct to a target gene of a nucleic acid of a cell;

(b) an actuating sequence that comprises a 3' splice acceptor (SA) followed by a reporter in sense orientation with respect to transcription of the target gene;
(c) a drug selection cassette (DSC) in sense or antisense orientation;
(d) a nucleotide sequence of interest (NSI) in anti sense orientation;
(e) a conditional by inversion (COIN) element in antisense orientation; and
(f) recombinable units comprising:
  (i) a first pair of cognate recombinase recognition sites, R1/R1';
  (ii) a second pair of cognate recombinase recognition sites, R2/R2';
  (iii) a third pair of cognate recombinase recognition sites, R3/R3';
  (iv) a fourth pair of cognate recombinase sites, R4/R4'; and
  (v) a fifth pair of cognate recombinase sites R5/R5';
  wherein R1/R1' and R3/R3' are recognized by a first recombinase, wherein R4/R4' and R5/R5' are recognized by a second recombinase, and wherein R2/R2' are recognized by a third recombinase, wherein the first, second, and third recombinases are not the same;
  wherein a first recombinable unit is framed by R1 and R1' in opposite orientation, wherein between R1 and R1' are disposed: the actuating sequence; R2; the DSC; R3; the NSI; R4, and R5;
  wherein a second recombinable unit is framed by recombinase sites R2 and R2' in the same orientation, wherein between R2 and R2' are disposed: the DSC; R3; the NSI; R4, R5; R1'; R3' in opposite orientation with respect to R3; the COIN element; R5' in the same orientation with respect to R5; R4' in the same orientation with respect to R4;
  wherein a third recombinable unit is framed by recombinase sites R3 and R3' in opposite orientation, wherein between R3 and R3' are disposed: the NSI; R4, R5; and R1';
  wherein a fourth recombinable unit framed by recombinase sites R4 and R4' in the same orientation, wherein between R4 and R4' are disposed; R5; R1'; R3'; the COIN element and R5';
  wherein a fifth recombinable unit is framed by R5 and R5' in the same orientation, wherein between R5 and R5' are disposed: R1'; R3'; and the COIN element; and
  wherein: (I) the recombinable units recombine upon exposure to the first recombinase to form a conditional allele that lacks the actuating sequence and the DSC, and contains the NSI in sense orientation and the COIN element in antisense orientation; and wherein the conditional allele when further exposed to the second recombinase, recombines to form an allele having the NSI in antisense orientation and having the COIN element in sense orientation; or (II) the recombinable units recombine upon exposure to the third recombinase to form a null allele that lacks the DSC, the NSI, and the COIN, and contains the actuating sequence in sense orientation.

2. The nucleic acid construct of claim 1, wherein the NSI is selected from the group consisting of:
  (a) a wild-type exon or exons of a gene;
  (b) an exon or exons of a gene having one or more nucleic acid substitutions, deletions, or additions;
  (c) an exon and neighboring intronic sequence;
  (d) a wild-type exon and neighboring intronic sequence;
  (e) an exon of a gene having one or more nucleic acid substitutions, deletions, or additions and neighboring intronic sequence; and
  (f) a human exon homologous to a mouse exon.

3. The nucleic acid construct of claim 1, wherein the reporter is selected from the group consisting of a fluorescent protein, a luminescent protein, and an enzyme.

4. The nucleic acid construct of claim 1, wherein the reporter is selected from the group consisting of GFP, eGFP, CFP, YFP, eYFP, BFP, eBFP, DsRed, MmGFP, luciferase, LacZ, and Alkaline Phosphatase.

5. The nucleic acid construct of claim 1, wherein the DSC comprises a sequence that encodes an activity selected from the group consisting of neomycin phosphotransferase ($neo^r$), hygromycin B phosphotransferase ($hyg^r$), puromycin-N-acetyltransferase ($puro^r$), blasticidin S deaminase ($bsr^r$), xanthine/guanine phosphoribosyl transferase (gpt), nourseothricin acetyltransferase (nat1), and Herpes simplex virus thymidine kinase (HSV-tk).

6. The nucleic acid construct of claim 1, wherein the COIN element comprises an exon of a gene that comprises one or more nucleic acid substitutions, deletions, or additions or comprises a 3' splice region.

7. The nucleic acid construct of claim 6, wherein the exon is an exon of a human, a mouse, a monkey, or a rat.

8. The nucleic acid construct of claim 6, wherein the 3' splice region is followed by a sequence selected from the group consisting of a cDNA, an exon-intron sequence, a microRNA, a microRNA cluster, a small RNA, a codon-skipping element, an IRES, a polyadenylation sequence, and a combination thereof.

9. The nucleic acid construct of claim 8, wherein the small RNA is a mirtron.

10. The nucleic acid construct of claim 8, wherein the codon-skipping element is T2A, E2A, or F2A.

11. The nucleic acid construct of claim 1, wherein the COIN element is selected from the group consisting of a second reporter, a SA-drug resistance cDNA-polyA, and a SA-reporter-polA.

12. The nucleic acid construct of claim 11, wherein the COIN element is the SA-drug resistance cDNA-polyA.

13. The nucleic acid construct of claim 11, wherein the COIN element is the SA-reporter-polyA.

14. The nucleic acid construct of claim 1, wherein the cognate recombinase recognition sites are selected from the group consisting of FRT sites, FRT3 sites, loxP sites, lox2372 sites, Rox sites, and attP/attB sites.

15. The nucleic acid construct of claim 1, wherein the first, second, and third recombinases are selected from the group consisting of Cre, Dre, PhiC31\int, and Flp.

* * * * *